US006210885B1

(12) United States Patent
Gjerde et al.

(10) Patent No.: US 6,210,885 B1
(45) Date of Patent: *Apr. 3, 2001

(54) MODIFYING DOUBLE STRANDED DNA TO ENHANCE SEPARATIONS BY MATCHED ION POLYNUCLEOTIDE CHROMATOGRAPHY

(75) Inventors: Douglas T. Gjerde, Saratoga; Paul D. Taylor; Robert M. Haefele, both of Palo Alto, all of CA (US)

(73) Assignee: Transgenomic, Inc., San Jose, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/169,440

(22) Filed: Oct. 9, 1998

Related U.S. Application Data

(60) Provisional application No. 60/103,313, filed on Oct. 6, 1998, provisional application No. 60/075,720, filed on Feb. 24, 1998, provisional application No. 60/063,906, filed on Oct. 31, 1997, and provisional application No. 60/061,445, filed on Oct. 9, 1997.

(51) Int. Cl.$^7$ .............................. C12Q 1/68; C12P 19/34; C07H 21/04; B01D 15/00; B11D 15/08
(52) U.S. Cl. .......................... 435/6; 435/91.1; 435/91.2; 536/23.1; 536/24.3; 536/24.31; 536/24.32; 536/25.3; 536/25.32; 510/198.2; 510/635; 510/656; 510/685
(58) Field of Search .................... 210/635, 656, 210/638, 198.2, 695, 654, 655, 660, 666, 684, 685; 536/23.1, 24.3, 24.31, 24.32, 24.33, 22.1, 25.3, 25.32; 435/6, 91.1, 91.2

(56) References Cited

U.S. PATENT DOCUMENTS

| | | | |
|---|---|---|---|
| 4,395,486 | 7/1983 | Wilson et al. ............................ | 435/6 |
| 4,656,127 | 4/1987 | Mundy ..................................... | 435/6 |
| 4,855,225 | 8/1989 | Fung et al. .............................. | 435/6 |
| 5,217,863 | 6/1993 | Cotton et al. ............................ | 435/6 |
| 5,550,025 | 8/1996 | Walker ..................................... | 435/6 |
| 5,585,236 | 12/1996 | Bonn et al. .............................. | 435/5 |
| 5,589,329 | 12/1996 | Winkler et al. .......................... | 435/5 |
| 5,670,325 | 9/1997 | Lapidus et al. .......................... | 435/6 |
| 5,698,397 | 12/1997 | Zarling et al. ........................... | 435/6 |
| 5,728,526 | 3/1998 | George, Jr. et al. ..................... | 435/6 |
| 5,763,162 | 6/1998 | Glazer et al. ............................ | 435/6 |
| 5,763,178 | 6/1998 | Chirikjian et al. ....................... | 435/6 |
| 5,772,889 | 6/1998 | Gjerde et al. ........................ | 210/635 |
| 5,789,588 | 8/1998 | Takenishi et al. .................... | 544/130 |
| 5,795,976 | * 8/1998 | Oefner et al. ....................... | 536/25.4 |
| 5,800,996 | 9/1998 | Lee et al. ................................. | 435/6 |
| 5,869,245 | 2/1999 | Yeung ..................................... | 435/6 |
| 5,986,085 | * 11/1999 | Gjerde et al. ....................... | 536/24.1 |
| 6,066,258 | * 5/2000 | Gjerde et al. ........................ | 210/635 |

FOREIGN PATENT DOCUMENTS

| | | | |
|---|---|---|---|
| 94/11305 | 5/1994 | (WO) | ............................... G02F/1/28 |
| 95/29258 | 11/1995 | (WO) | ............................... C12Q/1/68 |
| 98/40395 | 9/1998 | (WO) | ............................... C07H/21/04 |

OTHER PUBLICATIONS

Myers et al NAR vol. 13 pp. 3111–3129, 1985.*

Arguello et al. Mutation Detection and Typing of Polymorphic LOCI Through Double–Strand Confimation Analysis, Nature Genetics (1998) 18: 192–194.

Bischoff et al, Isolation of Specific TRNAS Using An Ionic–Hydrophobic Mixed–Mode Chromatographic Matrix, Analytical Biochemistry, 151: 526–533 (1985).

Brow et al, Cleavase Fragment Length Polymorphism Analysis for Mutation Scanning, Biomedical Products (Sep. 1997).

Cotton et al, Reactivity of Cytosine Ans Thymine in Single–Base–Pair Mismatches with Hydrozylamine an Osmium Tetroxide and its Application to the Stury of Mutations, Proc. Natl. Acad. Sci. USA, 85: 4397–4401 (Jun. 1988).

Cotton et al, Slowly by Surely Towards Better Scanning for Mutations, TIG, vol. 13 No. 2: 43–46 (Feb. 1997).

Ellis et al, Chemical Cleavage of Mismatch: A New Look at an Established Method, Human Mutation, 11: 345–353 (1998).

Hayward–Lester et al, Rapid Quantification of Gene Expression by Competitive PT–PCR and Ion–Pair Reversed–Phase HPLC, BioTechniques, 20: 250–257 (1996).

He et al. On–The–Fly Fluorescence Lifetime Detection of Dye–Labeled DNA Primers Fo Multiplex Analysis, Anal. Chem. (1997) 70: 3413–3418.

(List continued on next page.)

Primary Examiner—Kenneth R. Horlick
Assistant Examiner—Jeffrey Siew
(74) Attorney, Agent, or Firm—William B. Walker

(57) ABSTRACT

Covalently bound non-polar tags are used to increase the retention times of double stranded polynucleotides on Matched Ion Polynucleotide Chromatography (MIPC) columns. In doing so, separations of DNA mixture components is improved. Additionally, when the non-polar tags are fluorophores, detection limits are also greatly reduced. Strategically tagged primers are used in conduction with PCR to produce DNA fragments having specifically tagged strands. This improves mutation detection by MIPC in several ways. Separations are improved, detection sensitivity is enhanced, and non-stoichiometric addition of wild type DNA prior to hybridization is now possible since only tagged fragments will be observed with a fluorescence detector. Non-polar tags are also used as a novel alternative to G-C clamping during MIPC under partially denaturing conditions. Reversible DNA binding dyes, such as DNA intercalator dyes and DNA groove binding dyes, are used to reduce the detection limit of polynucleotides separated by MIPC.

29 Claims, 7 Drawing Sheets

OTHER PUBLICATIONS http://licor.com/bio/4200Page/4200App5.htm LI–COR, Inc. Mitation Screening, (Jun. 26, 1998).

http://www.mdyn.com/application_notes/AP54.htm Molecular Dynamics, Application Note 54, Two–Color Mutation Detection in 96–Well Microplates, (Oct. 15, 1997).

Huber et al., Micropellicular Stationary Phases for High–Performance Liquid Chromatography of Double–Stranded DNA, J. of Chromatography A (1997) 000: 000–000.

Kallioniemi et al. Detection of Mutations and Polymorphisms in DNA, 1997, CRC Press, ed. By Graham R. Taylor, USA pp. 273–285.

Mansfield et al. Two–Color Mutation Detection in 96–Well Microplates, Application Note 54, Molecular Dynamics web–site http://www.mdyn.com/application_notes/AP54.htm.

Mashal et al, Detection of Mutations by Cleavage of DNA Heteroduplexes with Bacteriophage Resolvases, Nature Genetics, 9: 177–183 (Feb. 1995).

Masahl et al, Practical Methods of Mutation Detection, Genetics & Development, 6: 275–280 (1998).

Myers et al. Genomic Analysis: A Practical Approach, IRL Press, K. Davis, ed. (1988) pp. 95–138.

Nunnally et al, Characterization of Visible Dyes For Four–Decay Fluorescence Detection in DNA Sequencing, Analytical Chemistry, 69: 2392–2397 (1997).

Oefner et al, High–Performance Liquid Chromatography for Routine Analysis of Hepatitis C Virus CDNA/PCR Products, Research Reports, vol. 16 No. 5 (1994).

Oefner et al, High–Resolution Liquid Chromatography of Fluorescent Dye–Labeled Nucleic Acids, Analytical Biochemistry, 223: 1–8 (1994).

Promega Corporation, Technical Bulletin Fluoro Amp Oligonucleotide Labeling System (Jul. 1994).

Promega Protocols and Applications Guide Third Edition, Cat.#P1610, 1996 pp. 147–162.

Rao et al, Direct Sequencing of Polymerase Chain Reaction—Amplified DNA Analytical Biochemistry, 216: 1–14 (1994).

Shi et al. Synthesis, Characterization and Luminescent Properties of EU111 and TB111 Fluorescent Chelated Used as Label in Medical Immunoassays, Journal of Alloys an Compounds, 207/208, pp. 29–32 1994.

Underhill et al, A Pre–Columbian Y Chrromosome–Specific Transition and Its Implications for Human Evolutionary History, Proc. Natl. Acad. Sci., 93: 196–200 (Jan. 1996).

* cited by examiner

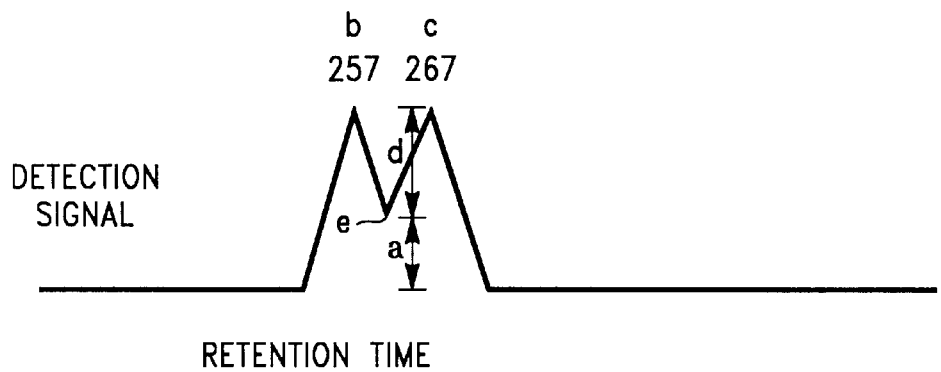
FIG.—1
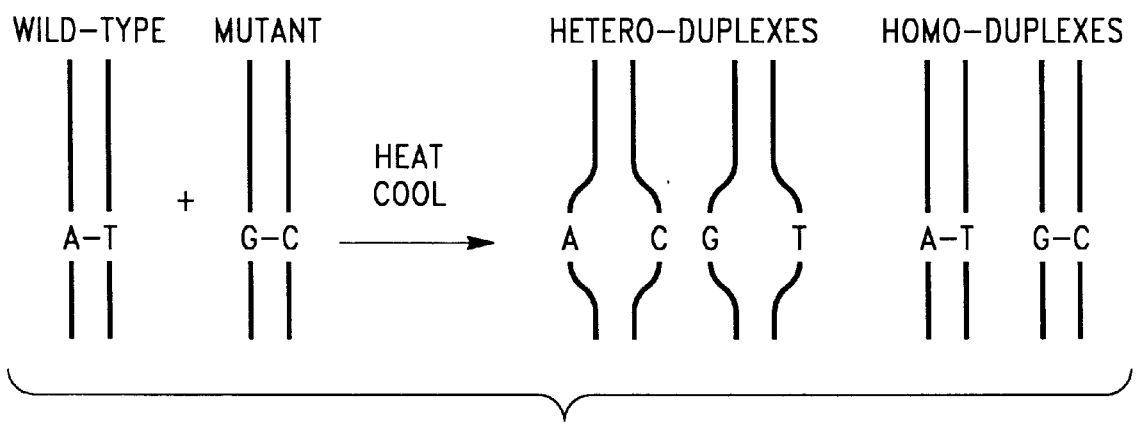
FIG.—4

MODIFYING DOUBLE STRANDED DNA TO ENHANCE SEPARATIONS BY MATCHED ION POLYNUCLEOTIDE CHROMATOGRAPHY

CROSS REFERENCE TO RELATED CO-PENDING APPLICATIONS

This application is a regular U.S. patent application under 35 U.S.C. §111(a) and 37 C.F.R. 1.53(b) and claims priority from the following co-pending, commonly assigned provisional applications, each filed under 35 U.S.C. §111(b):

Ser. No. 60/061,445 filed Oct. 9, 1997

Ser. No. 60/063,906 filed Oct. 31, 1997

Ser. No. 60/075,720 filed Feb. 24, 1998

Ser. No. 60/103,313 filed Oct. 6, 1998.

FIELD OF THE INVENTION

The present invention concerns the use of covalently attached chemical tags and reversibly bound dyes (e.g., intercalators) to enhance the separation and detection of polynucleotides separated by Matched Ion Polynucleotide Chromatography (MIPC). More specifically, the invention concerns the use of fluorescent tags and non-polar tags in MIPC separations of double stranded DNA in order to optimize and increase the sensitivity of mutation detection.

BACKGROUND OF THE INVENTION

Mixtures of double stranded nucleic acid fragments having different base pair lengths are separated for numerous and diverse reasons. The ability to detect mutations in double stranded polynucleotides, and especially in DNA fragments which have been amplified by PCR, presents a somewhat different problem since DNA fragments containing mutations are generally the same length as their corresponding wild type (defined herein below) but differ in base sequence.

DNA separation and mutation detection are of great importance in medicine, as well as in the physical and social sciences, as well as in forensic investigations. The Human Genome Project is providing an enormous amount of genetic information which is setting new criteria for evaluating the links between mutations and human disorders (Guyer, et al., *Proc. Natl. Acad. Sci. USA* 92:10841 (1995)). The ultimate source of disease, for example, is described by genetic code that differs from wild type (Cotton, *TIG* 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* 69:201 (1985)). Understanding these and other issues related to genetic coding is based on the ability to identify anomalies, i.e., mutations, in a DNA fragment relative to the wild type. A need exists, therefore, for a methodology which can separate DNA fragments based on size differences as well as separate DNA having the same length but differing in base pair sequence (mutations from wild type), in an accurate, reproducible, reliable manner. Ideally, such a method would be efficient and could be adapted to routine high throughput sample screening applications.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs, which after further replication of the new strand, results in double stranded DNA offspring containing a heritable difference in the base sequence from that of the parent. Such heritable changes in base pair sequence are called mutations.

In the present invention, double stranded DNA (dsDNA) is referred to as a duplex. When a base sequence of one strand is entirely complimentary to a base sequence of the other strand, the duplex is called a homoduplex. When a duplex contains at least one base pair which is not complimentary, the duplex is called a heteroduplex. A heteroduplex is formed during DNA replication when an error is made by a DNA polymerase enzyme and a non-complimentary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, it is generally called "wild type".

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein.

The sequence of base pairs in DNA code for the production of proteins. In particular, a DNA sequence in the exon portion of a DNA chain codes for the corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, *TIG* 13:43 (1997)).

Alterations in a DNA sequence which are benign or have no negative consequences are sometimes called "polymorphisms". In the present invention, any alterations in the DNA sequence, whether they have negative consequences or not, are called "mutations". It is to be understood that the method and system of this invention have the capability to detect mutations regardless of biological effect or lack thereof. For the sake of simplicity, the term "mutation" will be used throughout to mean an alteration in the base sequence of a DNA strand compared to a reference strand (generally, but not necessarily, wild type). It is to be understood that in the context of this invention, the term "mutation" includes the term "polymorphism" or any other similar or equivalent term of art.

There exists a need for an accurate and reproducible analytical method for mutation detection which is easy to implement. Such a method, which can be automated and provide high throughput sample screening with a minimum of operator attention, is also highly desirable.

Size based analysis of DNA samples has historically been done using gel electrophoresis (GEP). Capillary gel electrophoresis (CGE) has also been used to separate and analyze mixtures of DNA fragments having different lengths, e.g., the result of restriction enzyme cleavage. However, these methods cannot distinguish DNA fragments which differ in base sequence, but have the same base pair length. Therefore, gel electrophoresis cannot be used directly for mutation detection. This is a serious limitation of GEP.

Gel based analytical methods, such as denaturing gradient gel electrophoresis (DGGE) and denaturing gradient gel capillary electrophoresis (DGGC), can detect mutations in heteroduplex DNA strands under "partially denaturing" conditions. The term "partially denaturing" means the separation of a mismatched base pair (caused by temperature, pH, solvent, or other factors) in a DNA double strand while the remainder of the double strand remains intact. The phenomenon of "partial denaturation" is well known in the art and occurs because a heteroduplex will denature at the site of base pair mismatch at a lower temperature than is required to denature the remainder of the strand. However, these gel based techniques are operationally difficult to implement and require highly skilled personnel. In addition, the analyses are lengthy and require a great deal of set up time. A denaturing capillary gel electrophoresis analysis is limited to relatively small fragments. Separation of a 90 base pair fragment takes more than 30 minutes. A gradient denaturing gel runs overnight and requires about a day of set up time. Additional deficiencies of gradient gels are the isolation of separated DNA fragments (which requires specialized techniques and equipment) and analysis conditions must be experimentally developed for each fragment (*Laboratory Methods for the Detection of Mutations and Polymorphisms*, ed. G. R. Taylor, CRC Press, 1997). The long analysis time of the gel methodology is further exacerbated by the fact that the movement of DNA fragments in a gel is inversely proportional, in a geometric relationship, to their length. Therefore, the analysis time of longer DNA fragments can often be untenable.

Another problem encountered under partially denaturing conditions occurs when a mutation is located in a domain of a DNA fragment which has a high melting temperature relative to other domains of the same fragment. In such a case, partially denaturing conditions cannot be achieved since the entire double strand will denature before the site of base mismatch (mutation site) denatures. To circumvent this problem, a "G-C" clamp can be applied to a terminal domain of the DNA fragment as described by Myers, et al., in *Nucleic Acids Res.* 13:3111 (1985) and Sheffield, et al., in *Proc. Natl. Acad Sci. USA* 86:232 (1989) both of which publications are hereby incorporated by reference. A "G-C" clamp is a sequence of several G-C base pairs, generally 10–20, located at a terminus of the DNA fragment. Since G-C base pairs have stronger hydrogen bonds than those of other bases, their melting temperature is higher. Therefore, partial denaturing can occur at a mutation site, while the G-C clamp keeps the DNA strand from denaturing entirely. G-C clamps are introduced into DNA fragments by connecting a G-C sequence of desired length to a primer to be used in PCR amplification of a target DNA fragment. However, this an expensive and labor intensive technique.

In addition to the deficiencies of denaturing gel methods mentioned above, these techniques are not always reproducible or accurate since the preparation of a gel and running an analysis can be highly variable from one operator to another, and in general, suffer from serious deficiencies which are inherent to the art.

Separation of double stranded nucleic acid fragment mixtures by GEP or DGGE produces a linear array of bands, wherein each band in the array represents a separated double stranded nucleic acid component of that mixture. Since many mixtures are typically separated and analyzed simultaneously in separate lanes on the same gel slab, a parallel series of such linear arrays of bands is produced. Bands are often curved rather than straight, their mobility and shape can change across the width of the gel and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results. In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

Methods for visualizing GEP and DGGE separations, such as staining or autoradiography are also cumbersome and time consuming. In addition, separation data is in hard copy form and cannot be electronically stored for easy retrieval and comparison, nor can it be enhanced to improve the visualization of close separations. Fluorescent tags have been covalently attached to DNA fragments which have been separated on a gel in order to enhance detection of the separated DNA fragments (for example, U.S. Pat. No. 4,855, 255 (1989) to Fung). This reference in incorporated by reference herein in its entirety. However, this approach still suffers from the inherent disadvantages related to gel based separations described above.

Recently, an ion pairing reverse phase HPLC method was introduced to effectively separate mixtures of double stranded polynucleotides, in general and DNA, in particular, wherein the separations are based on base pair length. This method is described in the following references which are incorporated herein in their entireties: U.S. Pat. No. 5,795,976 (1998) to Oefner; U.S. Pat. No. 5,585,236 (1996) to Bonn; Huber, et al., *Chromatographia* 37:653 (1993); Huber, et al., *Anal. Biochem.* 212:351 (1993).

As the use and understanding of HPLC developed it became apparent that when HPLC analyses were carried out at a partially denaturing temperature, i.e., a temperature sufficient to denature a heteroduplex at the site of base pair mismatch, homoduplexes could be separated from heteroduplexes having the same base pair length as disclosed in the following references: Hayward-Lester, et al., *Genome Research* 5:494 (1995); Underhill, et al., *Proc. Natl. Acad. Sci. USA* 93:193 (1996); Oefner, et al., *DHPLC Workshop*, Stanford University, Palo Alto, Calif., (Mar. 17, 1997); Underhill, et al., *Genome Research* 7:996 (1997); Liu, et al., *Nucleic Acid Res.*, 26;1396 (1998). These references and the references contained therein are incorporated herein in their entireties. DHPLC can separate heteroduplexes that differ by as little as one base pair. However, as demonstrated in the these references, in certain cases, separations of homoduplexes and heteroduplexes are poorly resolved. Artifacts and impurities can interfere with the interpretation of DHPLC separation chromatograms in the sense that it may be difficult to distinguish between an artifact or impurity and a putative mutation. The presence of mutations may even be missed entirely.

The accuracy, reproducibility, convenience and speed of DNA fragment separations and mutation detection assays based on HPLC have been compromised in the past because of HPLC system related problems. Applicants have addressed these problems and applied the term "Matched Ion Polynucleotide Chromatography" (MIPC) to the separation method and system which is used in connection with the present invention. When used under partially denaturing conditions, MIPC is defined herein as Denaturing Matched Ion Polynucleotide Chromatography (DMIPC).

The term "Matched Ion Polynucleotide Chromatography" as used herein is defined as a process for separating single and double stranded polynucleotides using separation media having a non-polar surface, wherein the process uses a counterion agent, and an organic solvent to release the polynucleotides from the separation media. MIPC separations are routinely complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and column inlet areas. Non-limiting examples of key distinguishing features of MIPC include the a) use of hardware having liquid contacting surfaces which do not release multivalent cations therefrom, b) protection of liquid contacting surfaces from exogenous multivalent cations by means cartridges containing multivalent cation capture resins, c) the use of a special washing protocol for MIPC separation media, d) automated selection of an optimum solvent gradient solvent gradient for elution of a specific base length DNA fragment, and e) automated determination of the temperature required to effect partial denaturation of a heteroduplex when MIPC is used under partially denaturing conditions (DMIPC) for mutation detection.

Important aspects of DNA separation and mutation detection by HPLC and DHPLC which have been recognized and addressed by Applicants, comprise a) the treatment of, and materials comprising chromatography system components, b) the treatment of, and materials comprising separation media, c) solvent pre-selection to minimize methods development time, d) optimum temperature pre-selection to effect partial denaturation of a heteroduplex during HPLC and e) optimization of DHPLC for automated high throughput mutation detection screening assays. These factors, which comprise MIPC/DMIPC but not HPLC/DHPLC, are essential when using chromatographic methods in order to achieve unambiguous, accurate, reproducible and high throughput DNA separations and mutation detection results. A comprehensive description of MIPC systems and separation media, including the critical importance of maintaining an environment which is free of multivalent cations, is presented in U.S. Pat. No. 5,772,889 (1998) to Gjerde and U.S. patent application Ser. No. 09/129,105 filed Aug. 4, 1998; Ser. No. 09/081,040 filed May 18, 1998. Now U.S. Pat. No. 5,997,742; Ser. No. 09/080,547 filed May 18, 1998 now U.S. Pat. No. 6,017,457; Ser. No. 09/058,580 filed Apr. 10, 1998 now abandoned; Ser. No. 09/058,337 filed Apr. 10, 1998 now abandoned; Ser. No. 09/065,913 filed Apr. 24, 1998; Ser. No. 09/039,061 filed Mar. 13, 1998 now U.S. Pat. No. 5,986,913; Ser. No. 09/081,039 filed May 18, 1998 now U.S. Pat. No. 5,972,222. These references and the references contained therein are incorporated in their entireties herein.

DNA fragments which have been separated by MIPC or other chromatographic methods, have been detected using a uv detector set at the DNA absorption maximum of about 260 nm. Although generally effective, a detection method which is more sensitive than uv is often required. For example, when only very small amounts of sample are available or when trying to detect a DNA fragment in the presence of a very large excess of another fragment(s), e.g. cancer screening.

The use of radioactive labels is a well known method of detection in the DNA separation art. However, this method is costly, developing autoradiograms to visualize a separation is a very lengthy process, and radioactivity poses a health hazard.

A need exists, therefore, for a detection method which is capable of detecting DNA fragments at a lower threshold than uv, is not hazardous, and wherein the detection method is coupled to a separation system which allows for the efficient and reproducible separation of DNA fragments. Ideally, such a method is coupled to a system which can be automated for use in high throughput screening assays.

SUMMARY OF THE INVENTION

It is an object of the present invention to enhance the detection of a polynucleotide separated by Matched Ion Polynucleotide Chromatography. It is another object to improve the separation of polynucleotides in a mixture. It is still another object of the invention to increase to improve mutation detection in dsDNA by DMIPC.

In one aspect, the invention provides a method for enhancing the detection of a polynucleotide separated by Matched Ion Polynucleotide Chromatography which includes (a) covalently attaching a chemical tag to the polynucleotide to form a tagged polynucleotide, (b) applying the tagged polynucleotide to a separation medium having a non-polar separation surface, the medium characterized by having a DNA Separation Factor of at least 0.05, (c) eluting the tagged polynucleotide from the surface with a mobile phase containing a counterion agent and an organic solvent, and (d) detecting the tagged polynucleotide. The chemical tag is preferably a fluorescent group, a chemical which absorbs at a wavelength different from the polynucleotide itself, or, less preferably, a group containing a radioactive atom (e.g., P-32, tritium, or S-35). Non-limiting examples of fluorescent groups which absorb at a wavelength different from the polynucleotide itself include 5-carboxyfluorescein, 2',7'-dimethoxy-4',5'-dichloro-6-carboxyfluorescein, N,N,N',N'-tetramethyl-6-carboxyrhodamine, 6-carboxy-X-rhodamine, Fluorescein, Rhodamine, BODIPY-TR-X, Cascade Blue, Alexa 350, and porphyrin derivatives (e.g., texaphyrin). Non-limiting examples of fluorescent groups include 5-carboxyfluorescein, 2',7'-dimethoxy-4',5'-dichloro-6-carboxyfluorescein, N,N,N', N'-tetramethyl-6-carboxyrhodamine, 6-carboxy-X-rhodamine, Fluorescein, Rhodamine, BODIPY-TR-X, Cascade Blue, and Alexa 350. The preferred separation medium is characterized by having a Mutation Separation Factor of at least 0.1. The preferred medium is substantially free from contamination with multivalent cations. In one embodiment, the separation medium consists of polymer beads having an average diameter of 0.5 to 100 microns and having a surface composition essentially completely substituted with a moiety selected from the group consisting of unsubstituted, methyl, ethyl, hydrocarbon, and hydrocarbon polymer, wherein the hydrocarbon polymer optionally has from 23 to 1,000,000 carbons, wherein the hydrocarbon includes alkyl and alkyl substituted aryl groups having from 23 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. In another embodiment, the separation medium consists of beads having an average diameter of 0.5 to 100 microns, the beads comprising nonporous particles coated with a hydrocarbon or non-polar hydrocarbon substituted polymer, wherein the hydrocarbon has optionally from 1 to 1,000,000 carbons, wherein the hydrocarbon polymer has optionally from 1 to 1,000,000 carbons, or particles having substantially all polar groups reacted with a non-polar hydrocarbon or substituted hydrocarbon group, wherein the particles are a member selected from the group consisting of silica, silica carbide, silica nitrite, titanium oxide, aluminum oxide, zirconium oxide, carbon, insoluble polysaccharide, and diatomaceous earth. In other embodiments, the separation medium is a polymeric monolith or a derivatized silica gel monolith. The tagged polynucleotide can be a PCR amplification product obtained by providing a PCR primer having a covalently bound tag during a PCR amplification wherein the tag is incorporated into the PCR amplification product.

In another aspect, the invention provides a method for enhancing the detection of a polynucleotide separated by Matched Ion Polynucleotide Chromatography including (a) covalently attaching a chemical tag to the polynucleotide to form a tagged polynucleotide, (b) applying the tagged polynucleotide to a separation bed of Matched Ion Polynucleotide Chromatography particles, (c) eluting the tagged polynucleotide from the particles with a mobile phase containing a counterion agent and an organic solvent and (d) detecting the tagged polynucleotide, wherein steps (b) and (c) are performed in a system for separating a mixture of polynucleotide fragments comprising a chromatographic column having two ends, the column containing the separation bed of Matched Ion Polynucleotide Chromatography separation particles are held in the column between porous frits positioned at each end thereof, the column having an inlet, an injection valve in communication with the inlet through a flow path therebetween, mobile phase supply means in communication with the injection valve through at least one flow path therebetween, and multivalent cation capture resin, selected from cation exchange resin and chelating resin, positioned in the flow path, the multivalent cation capture resin being capable of removing multivalent cations from aqueous solutions, whereby any multivalent cation contaminants in the flow path are removed before the contaminants contact the separation bed.

In yet another aspect, the invention provides a method for enhancing the detection of a polynucleotide separated by Matched Ion Polynucleotide Chromatography. The method includes (a) covalently attaching a chemical tag to the polynucleotide to form a tagged polynucleotide, (b) applying the tagged polynucleotide to a separation bed of Matched Ion Polynucleotide Chromatography particles, (c) eluting the tagged polynucleotide from the particles with a mobile phase containing a counterion agent and an organic solvent and (d) detecting the tagged polynucleotide, wherein steps (b) and (c) are performed in a system for separating a mixture of polynucleotide fragments, the system comprising a chromatographic column having two ends, the column containing a separation bed of Matched Ion Polynucleotide Chromatography separation particles held in the column between porous frits positioned at each end thereof, the column having an inlet, an injection valve in communication with the inlet through a conduit, eluant supply means in communication with the injection valve through at least one conduit, wherein the porous frits, chromatographic column, injection valve, eluant supply means, and conduits have process solution-contacting surfaces which contact process solutions held therein or flowing therethrough, and wherein the process solution-contacting surfaces of the porous frits are material which does not release multivalent cations into aqueous solutions flowing therethrough.

In still another aspect, the invention provides a method for increasing the retention time of a polynucleotide separated by Matched Ion Polynucleotide Chromatography. This method includes (a) covalently attaching a chemical tag to the polynucleotide to form a tagged polynucleotide wherein the chemical tag is non-polar, (b) applying the tagged polynucleotide to a separation medium having a non-polar surface, (c) eluting the tagged polynucleotide from the surface with a mobile phase containing a counterion agent and an organic solvent and (d) detecting the tagged polynucleotide. The separation medium is characterized by having a DNA Separation Factor of at least 0.05. An example of a non-polar tag includes a hydrocarbon group, wherein the hydrocarbon group is selected from the group consisting of alkyl, cycloalkyl, aryl and arylalkyl groups. The number of carbon atoms in the hydrocarbon group can be up to about 18. Alkyl groups having up to 8 carbon atoms are preferred.

In an important aspect, the invention provides a method for enhancing the detection of a polynucleotide separated by Matched Ion Polynucleotide Chromatography, including (a) contacting the polynucleotide with a reversible DNA-binding dye to form a complex between the polynucleotide and the reversible DNA-binding dye, (b) applying the complex to a separation medium having a non-polar surface, (c) eluting the complex from the surface with a mobile phase containing a counterion agent and an organic solvent, and (d) detecting the complex. Preferred reversible DNA-binding dyes includes DNA intercalator dyes and DNA groove binding dyes. Non-limiting examples of reversible DNA-binding dyes include PICO GREEN, ethidium bromide, propidium iodide, Acridine orange, 7-aminoactinomycin D, cyanine dyes, Bisbenzimide, Bisbenzimide, Benzoxanthene yellow, Netropsin, SYTO, SYBR Green I, SYBR Green II, SYBR DX, OliGreen, CyQuant GR, SYTOX Green, SYTO9, SYTO10, SYTO17, SYBR14, FUN-1, DEAD Red, Hexidium Iodide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, and LDS 751.

In still yet another aspect, the invention concerns a method for the detection of a mutation in a sample double stranded DNA fragment. This method includes (a) covalently attaching a chemical tag to the sample DNA fragment or to a corresponding wild type fragment to form a tagged polynucleotide, (b) hybridizing the sample DNA fragment with the corresponding wild type DNA fragment to form a mixture of homoduplexes and heteroduplexes if a mutation is present in the sample DNA fragment, (c) applying the product of step (b) to a separation medium having a non-polar surface, (d) eluting the mixture with a mobile phase containing a counterion agent and an organic solvent where the eluting is carried out under conditions effective to at least partially denature the heteroduplexes and where the eluting results in the separation of the heteroduplexes from the homoduplexes, and (e) detecting the tagged polynucleotide. In one embodiment of this method, a different uniquely detectable tag is covalently attached to each strand of the sample DNA. In another embodiment, a different uniquely detectable chemical tag is covalently attached to each strand of the wild type fragment. In a preferred embodiment of this aspect, the separation medium is characterized by having a Mutation Separation Factor of at least 0.1. In one embodiment of this aspect of the invention, in step (b) the amount of the wild type fragment is added in excess of the sample DNA.

In a further aspect, the invention concerns a method for increasing the melting temperature of a double stranded DNA as determined by temperature titration using Matched Ion Chromatography, comprising covalently attaching a non-polar chemical tag to the polynucleotide to form a tagged polynucleotide prior to performing said temperature titration. The temperature titration is performed by (a) applying the tagged polynucleotide to a separation medium having a non-polar separation surface, (b) eluting the tagged polynucleotide from the surface with a mobile phase containing a counterion agent and an organic solvent, and (c) detecting the tagged polynucleotide, wherein steps (a) and (b) are performed at a plurality of temperatures above and below the melting temperature. The tagged polynucleotide. An example of a non-polar tag includes a hydrocarbon group, wherein the hydrocarbon group is selected from the group consisting of alkyl, cycloalkyl, aryl and arylalkyl groups. The number of carbon atoms in the hydrocarbon group preferably range up to about 18. Alkyl groups having up to 8 carbon atoms are most preferred. The tag can be a fluorescent group and is preferably bound at an end of the double stranded DNA.

In a further aspect, the invention is a method for detecting a chemically tagged polynucleotide separated by Matched Ion Polynucleotide Chromatography which includes the steps of (a) applying the tagged polynucleotide to a separation medium having a non-polar surface, (b) eluting the tagged polynucleotide from the surface with a mobile phase containing a counterion agent and an organic solvent and (c) detecting the tagged polynucleotide, wherein the separation medium is characterized by having a DNA Separation Factor of at least 0.05. In a preferred embodiment, the tag consists of a fluorescent group. Alternatively, the tag is a moiety that absorbs at a wavelength different from the polynucleotide. In a preferred embodiment, the separation medium is characterized by having a Mutation Separation Factor of at least 0.1. The preferred separation medium is substantially free from contamination with multivalent cations.

BRIEF DESCRIPTION OF THE DRAWINGS

FIG. 1 is a schematic representation of determination of the DNA Separation Factor.

FIG. 4 is a schematic showing the hybridization of sample and wild type to form a homoduplex/heteroduplex mixture.

FIG. 5 is a schematic showing the hybridization of a non-polar tagged wild type with a putative mutation containing sample and the relative retention times of the fragments separated by DMIPC.

FIG. 6 is a schematic showing the hybridization of a non-polar tagged wild type with a sample that does not contain a mutation and the relative retention times of the fragments separated by DMIPC.

FIG. 7 is a schematic showing the hybridization of an excess of a putative mutation containing sample with non-polar tagged wild type and the relative retention times of the fragments separated by DMIPC.

FIG. 8 is a schematic identical to FIG. 6 except that the sample does not contain a mutation.

FIG. 9 is a schematic showing the hybridization of a non-polar tagged putative mutation containing sample with an excess of wild type and the relative retention times of the fragments separated by DMIPC.

FIG. 10 is a schematic showing the hybridization of a non-polar tagged putative mutation containing sample with a non-polar tagged wild type, each fragment having the same non-polar tag, and the relative retention times of the fragments separated by DMIPC.

FIG. 11 is a schematic showing the hybridization of a non-polar tagged putative mutation containing sample with a non-polar tagged wild type, each fragment having a different non-polar tag, and the relative retention times of the fragments separated by DMIPC.

FIG. 12 is a schematic showing the hybridization of a non-polar tagged putative mutation containing sample with a non-polar tagged wild type, each strand having a different non-polar tag, and the relative retention times of the fragments separated by DMIPC.

DETAILED DESCRIPTION OF THE INVENTION

Figure 2:
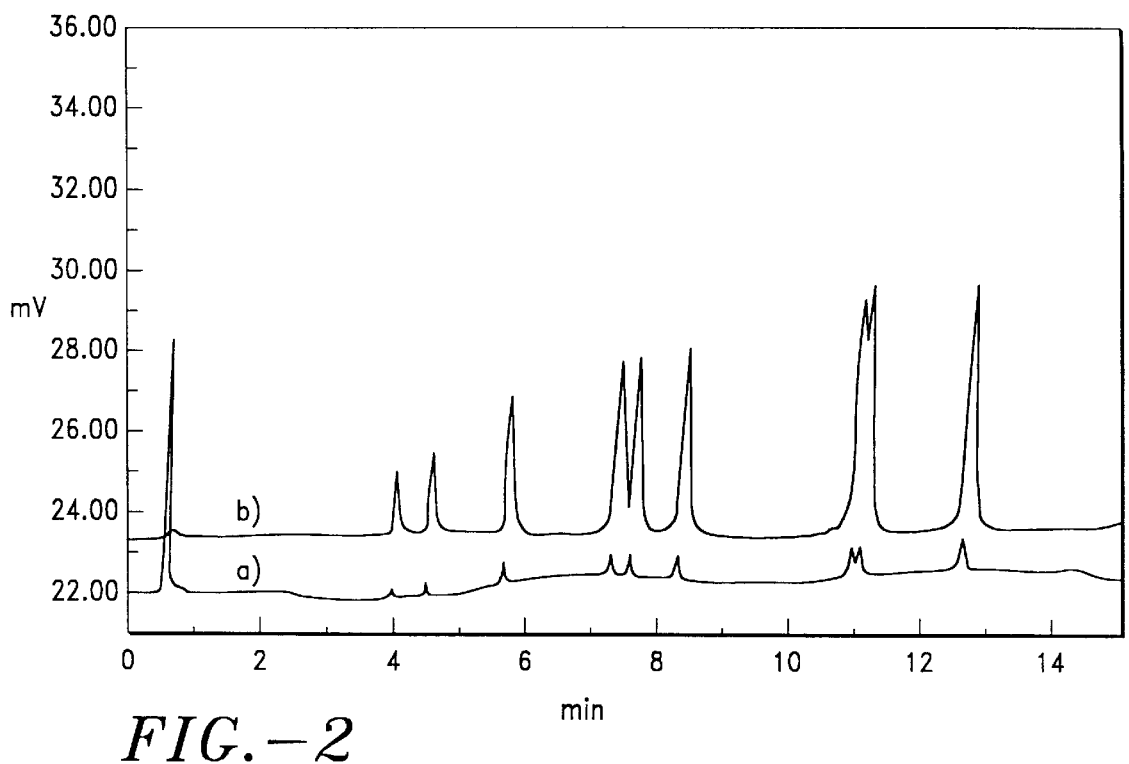
FIG. 2 is (a) a uv MIPC chromatogram, and (b) an intercalated PICO GREEN fluorescent MIPC chromatogram, of a pUC18 DNA-Hae III digest (D-6293, Sigma Chemical Co., St. Louis, Mo.).

In its most general form, the invention provides an improved method for separating and detecting polynucleotides. The term polynucleotide is defined as a linear polymer containing an indefinite number of nucleotides, linked from one ribose (or deoxyribose) to another via phosphoric residues. The present invention can be used in the separation of RNA or of double- or single-stranded DNA. For purposes of simplifying the description of the invention, and not by way of limitation, the separation of double-stranded DNA will be described in the examples herein, it being understood that all polynucleotides are intended to be included within the scope of this invention.

In its most general form, the subject matter of the present invention concerns the separation of polynucleotides. e.g. DNA, utilizing a stationary separation medium having non-polar surfaces. The preferred surfaces are essentially free from multivalent cation contamination which can trap polynucleotides. The separation is performed on the stationary surface. The surface can be porous, but preferably any surface pores are of a size which excludes the smallest polynucleotide being analyzed.

The medium can be enclosed in a column. In one embodiment, the non-polar surfaces comprise the surfaces of separation beads, such as polymeric beads or derivatized particles (e.g., silica particles). In an alternative embodiment, the surfaces comprise the surfaces of interstitial spaces in a molded monolith such as a polymeric monolith or a silica gel monolith. For purposes of simplifying the description of the invention and not by way of limitation, the separation of polynucleotides using nonporous beads, and the preparation of such beads, will be primarily described herein, it being understood that other separation surfaces, such as the surfaces within interstitial spaces of monoliths, are intended to be included within the scope of this invention. Examples of suitable monoliths include polymeric rods and derivatized silica gel rods which have been formed inside a column as a unitary structure having through pores or interstitial spaces which allow eluting solvent and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

In one aspect, the subject matter of the present invention is the separation of polynucleotides utilizing columns filled with nonporous polymeric beads having an average diameter of about 0.5–100 microns; preferably, 1–10 microns; more preferably, 1–5 microns. Beads having an average diameter of 1.0–3.0 microns are most preferred.

In U.S. Pat. No. 5,585,236, Bonn et al. had characterized the nucleic acid separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counterion agent, and an organic solvent to elute the nucleic acid from the beads, and wherein the beads are characterized as having a DNA Separation Factor of at least 0.05. In a preferred embodiment, the beads have a DNA Separation Factor of at least 0.5. In an optimal embodiment, the beads have a DNA Separation Factor of at least 0.95.

The performance of the beads (or other separation media) of the present invention is demonstrated by high efficiency separation by MIPC of double stranded and single stranded DNA. Applicants have found that a useful criterion for measuring performance of the beads is a "DNA Separation Factor." This is measured as the resolution of 257- and 267-base pair double stranded DNA fragments of a pUC18 DNA-HaeIII restriction digest and is defined as the ratio of the distance from the valley between the peaks to the top of the peaks, over the distance from the baseline to the top of the peaks. Referring to the schematic representation of FIG. 1, the DNA Separation Factor is determined by measuring the distance "a" from the baseline to the valley "e" between the peaks "b" and "c" and the distance "d" from the valley "e" to the top of one of the peaks "b" or "c". If the peak heights are unequal, the highest peak is used to obtain "d." The DNA Separation Factor is the ratio of d/(a+d). The peaks of 257- and 267-base pairs in this schematic representation are similar in height. A more detailed description of the determination of the DNA Separation Factor of separation media is provided below in Example 5 Operational beads of the present invention have a DNA Separation Factor of at least 0.05. Preferred beads have a DNA Separation Factor of at least 0.5.

Without wishing to be bound by theory, Applicants believe that the beads which conform to the DNA Separation Factor as specified herein have a pore size which essentially excludes the polynucleotides being separated from entering the bead. As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required. Preferably, all beads which provide a DNA Separation Factor of at least 0.5 are intended to be included within the definition of "nonporous" beads.

The surface conformations of nonporous beads (or other separation media) of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the resolution of separations or result in separations that have very long retention times. In MIPC, however, the beads are "nonporous" and the polynucleotides do not enter the bead structure.

Chromatographic efficiency of the column beads is predominantly influenced by the properties of surface and near-surface areas. For this reason, the following descriptions are related specifically to the close-to-the-surface region of the separation beads. The main body and/or the center of such beads can exhibit entirely different chemistries and sets of physical properties from those observed at or near the surface of the beads of the present invention.

In another embodiment of the present invention, the separation medium can be in the form of a polymeric monolith such as a rod-like monolithic column. The monolithic column is polymerized or formed as a single unit inside of a tube. The through pore or interstitial spaces provide for the passage of eluting solvent and analyte materials. The separation is performed on the stationary surface. The surface can be porous, but is preferably nonporous. The form and function of the separations are identical to columns packed with beads. As with beads, the pores contained in the rod must be compatible with DNA and not trap the material. Also, the rod must not contain contamination that will trap DNA.

The molded polymeric rod of the present invention is prepared by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly (glycidyl methacrylate-co-ethylene dimethacrylate), poly (styrene-divinylbenzene) and poly(ethylvinylbenzene-divinylbenzene. The rod can be unsubstituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (*J. Chromatog.* A 699:230 (1994)), Petro et al. (*Ana. Chem.* 68:315 (1996)), and the following U.S. Pat. Nos. 5,334,310; 5,453,185; 5,522,994 (to Frechet). Monolith or rod columns are commercially available form Merck & Co (Darmstadt, Germany).

The nonporous polymeric beads of the present invention are prepared by a two-step process in which small seed beads are initially produced by emulsion polymerization of suitable polymerizable monomers. The emulsion polymerization procedure of the invention is a modification of the procedure of Goodwin, et al. (*Colloid & Polymer Sci.,* 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example. The term hydrocarbon as used herein in reference to the polymer beads of the present invention is defined to include the group consisting of unsubstituted, methyl, ethyl, hydrocarbon, and hydrocarbon polymer, wherein the hydrocarbon polymer optionally has from 23 to 1,000,000 carbons, wherein the hydrocarbon includes alkyl and alkyl substituted aryl groups having from 23 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

The chromatographic material reported in the Bonn patent was limited to nonporous beads substituted with alkyl groups having at least 3 carbons because Bonn et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

In the present invention, it has now been surprisingly discovered that successful separation by MIPC of dsDNA, tagged polynucleotides, and intercalator dye-polynucleotide complexes can be achieved using underivatized nonporous beads as well as using derivatized beads.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, must provide a nonporous, non-reactive, and non-polar surface for the MIPC separation.

In another embodiment of the present invention, the separation medium is continuous monolithic silica gel. A molded monolith can be prepared by polymerization within the confines of a chromatographic column (e.g., to form a rod) or other containment system. A monolith is preferably obtained by the hydrolysis and polycondensation of alkoxysilanes. A preferred monolith is derivatized in order to produce non-polar interstitial surfaces. Chemical modification of silica monoliths with ocatdecyl, methyl or other ligands can be carried out. An example of a preferred derivatized monolith is one which is polyfunctionally derivatized with octadecylsilyl groups. The preparation of derivatized silica monoliths is by conventional methods well known in the art as described in the following references which are hereby incorporated in their entirety herein: Nakanishi, et al., *J. Sol-Gel Sci. Technol.* 8:547 (1997); Nakanishi, et al., *Bull, Chem. Soc. Jpn.* 67:1327 (1994); Cabrera, et al., *Trends Analytical Chem.* 17:50 (1998); Jinno, et al., *Chromatographia* 27:288 (1989).

In another embodiment of the separation medium of the invention, the beads of the invention comprise a nonporous particle which has non-polar molecules or a non-polar polymer attached to or coated on its surface. In general, the beads comprise nonporous particles which have been coated with a polymer or which have substantially all surface substrate groups reacted with a non-polar hydrocarbon or substituted hydrocarbon group, and any remaining surface substrate groups endcapped with a tri(lower alkyl) chlorosilane or tetra(lower alkyl)dichlorodisilazane as described above. The nonporous particle is preferably an inorganic particle, but can be a nonporous organic particle. The nonporous particle can be, for example, silica, silica carbide, silica nitrite, titanium oxide, aluminum oxide, zirconium oxide, carbon, insoluble polysaccharides such as cellulose, or diatomaceous earth, or any of these materials which have been modified to be nonporous. Examples of carbon particles include diamond and graphite which have been treated to remove any interfering contaminants. The preferred particles are essentially non-deformable and can withstand high pressures. The nonporous particle is prepared by known procedures. The preferred particle size is about 0.5–100 microns; preferably, 1–10 microns; more preferably, 1–5 microns. Beads having an average diameter of 1.0–3.0 microns are most preferred. Because the chemistry of preparing conventional silica-based reverse phase HPLC materials is well-known, most of the description of the beads of the invention herein is presented in reference to silica. It is to be understood, however, that other nonporous particles, such as those listed above, can be modified in the same manner and substituted for silica in the process of the invention. For a description of the general chemistry of silica, see Poole, Colin F. and Salwa K. Poole, *Chromatography Today*, Elsevier:New York (1991), pp. 313–342 and Snyder, R. L. and J. J. Kirkland, *Introduction to Modern Liquid Chromatography*, 2nd ed., John Wiley & Sons, Inc.:New York (1979), pp. 272–278, the disclosures of which are hereby incorporated herein by reference in their entireties.

The nonporous silica beads of the invention are characterized by having minimum exposed silanol groups after reaction with the coating or silating reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column. Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based mobile phase. Hydrolysis will increase the polarity and reactivity of the stationary phase by exposing more silanol sites, or by exposing metals that can be present in the silica core. Hydrolysis will be more prevalent with increased underivatized silanol groups. The effect of silanol groups on the DNA separation depends on which mechanism of interference is most prevalent. For example, iron (III) can become attached to the exposed silanol sites, depending on whether the iron (III) is present in the eluent, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8 $\mu$moles of silanol groups per square meter of surface. At best, because of steric considerations, a maximum of about 4.5 $\mu$moles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1–2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. Iler in *The Chemistry of Silica, Solubility, Polymerization, Colloid and Surface Properties, and Biochemistry*, John Wiley & Sons:New York (1979).

W. Stöber et al. described controlled growth of monodisperse silica spheres in the micron size range in *J. Colloid and Interface Sci.*, 26:62–69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 $\mu$m to 2 $\mu$m in diameter.

Nonporous silica core beads can be obtained from Micra Scientific (Northbrook, Ill.) and from Chemie Uetikkon (Lausanne, Switzerland).

To prepare the nonporous silica beads of the invention, the nonporous particle is coated with a polymer or reacted and endcapped so that substantially all surface substrate groups of the nonporous particle are blocked with a non-polar hydrocarbon or substituted hydrocarbon group. This can be accomplished by several methods.

The organic bonded-phase siloxane coating can be made as a monomolecular layer or as a polymerized multilayer coating. Packings with so-called monomolecular organic layers are normally prepared by reacting the surface silanol groups of siliceous-base particles with mono-, di-, or trifunctional chloro-, dimethyl-, amino-, siloxy-, or alkoxysilanes. Typical monofunctional reactants used in these reactions include X—Si—R, where X=Cl, OH, OCH$_3$, or OC$_2$H$_5$, and R is an organic radical.

Using bi- and trifunctional reactants, such as R$_2$SiX$_2$ and RSiX$_3$, for the surface modifications, up to two Si—X groups per bonded functional group remain unreacted. After treatment with water, hydrolysis of these unreacted groups takes place, and additional silanol groups are formed (sometimes in a polymer matrix) in about the same concentration as the bonded organic functional groups present in the packing. These acidic organo-silanol groups can significantly affect the retention behavior of solutes and adversely influence the stability of the packing in aqueous solutions at pH>7.

Thus, incomplete reaction of the surface with the silane reagent, or the formation of new Si—OH groups from using bi- or trifunctional modifiers, can result in a population of residual acidic Si—OH groups that are readily accessible to molecules of the mobile phase or sample. Therefore, the recent trend is toward (a) a dense monolayer of functional groups instead of partial coverage and (b) the use of monofunctional dimethylsilanes [X—Si(CH$_3$)$_2$—R] to provide a homogeneous organic coating with a minimum possibility of residual Si—OH groups. Monochlorosilane reagents are preferred, if the required organic functionality can be prepared. If two of the R groups in the monofunctional modifier are methyl, surface coverage can be as high as about 4 $\mu$moles per square meter of organic (based on carbon analysis). In the latter case, residual Si—OH groups on the silica surface are unavailable for chromatographic interactions with most solutes because of steric shielding.

The reaction of organosilanols (e.g., HO—Si—R$_3$) or organoalkoxy- (e.g., RO—Si—R$_3$) silanes with silica supports without polymerization can also produce good packings. These reactions are relatively reproducible, provided that traces of water or other reactive species are absent. Unreacted, accessible silanols can be left after the initial reaction, but these can be removed by capping of the packing with chlorotrimethylsilane (providing the R groups do not react with the latter silane).

According to one method, the nonporous particle is coated with a polymer coating. Suitable polymers for use in coating the particle include chain reaction polymers and step reaction polymers, for example, polystyrene, polymethacrylate, polyethylene, polyurethane, polypropylene, polyamide, insoluble polysaccharides such as cellulose, polydimethyl siloxane, polydialkyl siloxane, and related materials. The polymer coating can be attached to the nonporous particle by means of a multi-coating process so that complete shielding of the surface is achieved.

In the last few years, new bonded phase packings, known as polymer-coated or polymer-encapsulated packings, have been introduced based on techniques used to prepare immobilized stationary phases for open tubular column gas chromatography. In this case, the phases are prepared by mechanically coating either bare silica or presilanized silica microparticles with a poly(siloxane) or poly(butadiene) prepolymer, which is then immobilized by peroxide, azotert-butane, or gamma radiation-induced chemical crosslinking reactions.

An alternative method comprises a combination of covalent bonding with a vinyl-containing silane molecule and then polymerizing a coating on the surface of the particles. A second coating can be applied if residual silanol groups or metal groups are present.

In a variation of this method, the silica surface is first modified by reaction with vinyltrichlorosilane, followed by polymerizing acrylic acid derivatives to and over the derivatized silica surface. The availability of a large number of useful monomers and prepolymers has enabled a wide variety of reverse phase, polar, and ion exchange packings to be prepared using the same general reaction. Also, since the general approach does not depend on the chemistry of the underlying substrate, materials other than silica, for example, alumina and zirconia, can be modified and used under conditions for which silica is unsuitable, for example, with mobile phases outside the pH range 2–7.5. Returning to silica, presilanization decreases the number of active silanol groups, which are then further shielded by the polymeric film anchored over the surface. In reverse phase liquid chromatography, these packings have shown improved chromatographic properties compared to monomeric, chemically bonded phases for the separation of basic solutes. Polymer-encapsulated packings have a film thickness of about 1 nm to maintain reasonable mass transfer characteristics. A description of the this procedure has been published by H. Engelhart et al. (*Chromatographia,* 27:535 (1989)).

The polymer-coated beads prepared according to either of the above methods can be used in their unmodified state or can be modified by substitution with a hydrocarbon group. Any hydrocarbon group is suitable. The term "hydrocarbon" as used herein is defined to include alkyl and alkyl substituted aryl groups, having from 1 to 1,000,000 carbons, the alkyl groups including straight chained, branch chained, cyclic, saturated, unsaturated nonionic functional groups of various types including, aldehyde, ketone, ester, ether, alkyl groups, and the like, and the aryl groups including as monocyclic, bicyclic, and tricyclic aromatic hydrocarbon groups including phenyl, naphthyl, and the like. Methods for hydrocarbon substitution are conventional and well-known in the art and are not an aspect of this invention. The hydrocarbon can also contain hydroxy, cyano, nitro groups, or the like which are considered to be non-polar, reverse phase functional groups. The preferred hydrocarbon groups are alkyl groups, and the description of suitable substitution processes hereinbelow are presented as alkylation for purposes of simplification and not by way of limitation, it being understood that aryl substitution by conventional procedures are also intended to be included within the scope of this invention.

The polymer-coated beads can be alkylated by reaction with the corresponding alkyl halide such as the alkyl iodide. Alkylation is achieved by mixing the polymer-coated beads with an alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. Substitution with hydrocarbon groups having from 1 to 1,000,000 and preferably from 1 to 22 carbons can be effected by these processes. Hydrocarbon groups having from 23 to 1,000,000 carbons are referenced in this embodiment as hydrocarbon polymers.

Alkylation can be accomplished by a number of known synthesis procedures. These include Friedel-Crafts alkylation with an alkyl halide, attachment of an alkyl alcohol to a chloromethylated bead to form an ether, etc. Although the preferred method for alkylating the polymer-coated beads of the present invention is alkylation after the polymer coating has been formed on the nonporous particle, an alternative method of alkylation is to polymerize alkylated monomers to form an alkylated polymer coating on the nonporous particle. In this embodiment, the monomers will be substituted with alkyl groups having any number of carbon atoms, for example, from 1 to 100, 1 to 50 or 1 to 24, for example, depending upon the requirements of the separation variables.

As an alternative to polymer coating, the nonporous particle can be functionalized with an alkyl group or other non-polar functional group including cyano, ester, and other non-ionic groups, followed by a complete endcapping process to reduce silanol and metal interaction. Endcapping of the nonporous particle can be achieved by reacting the particle with trialkyl chlorosilane or tetraalkyl dichlorodisilazane, such as, for example, trimethyl chlorosilane or dichloro-tetraisopropyl-disilazane.

A large number of factors influence the success of the bonding reactions and the quality of the final bonded-phase product. The rate and extent of the bonding reaction depends on the reactivity of the silane, choice of solvent and catalyst, time, temperature, and the ratio of reagents to substrate. Reactive organosilanes with Cl, OH, OR, $N(CH_3)_2$, $OCOCF_3$, and enolates as leaving groups have been widely used. The dimethylamine, trifluoroacetate, and enol ethers of pentane-2,4-dione are the most reactive leaving groups, although economy, availability, and familiarity result in the chlorosilanes and alkoxysilanes being the most widely used, particularly among commercial manufacturers. Initially, reactions can be almost stoichiometric but, as the surface coverage approaches a maximum value, the reaction becomes very slow. For this reason, reaction times tend to be long (12–72 hours), reaction temperatures moderately high (in most cases, around 100° C.) and, in the case of chlorosilanes, an acid acceptor catalyst (e.g., pyridine) is used. Some reagents, such as the alkylsilyl enolates and alkylsilyldimethylamines, do not require additional catalyst, or even solvent, to carry out the reaction. The most common solvents employed are toluene and xylene, although other solvents, such as carbon tetrachloride, trichloroethane, and dimethylformamide (DMF), have been recommended as being superior. Since the bonding reactions are carried out by refluxing in an inert atmosphere, solvents are often selected based on their capacity to be a good solvent for the organosilanes and to attain the desired reaction temperature at reflux. Except for 3-cyanopropylsiloxane bonded phases, the high reactivity of chlorosilanes towards certain polar functional groups (e.g., OH, etc.) precludes the use of these groups for the preparation of polar, reverse phase bonded phases. Alkoxysilanes containing acidic or basic functional groups are autocatalytic and the bonded phases are usually prepared by refluxing the silane in an inert solvent at a temperature high enough to distill off the alcohol formed by the condensation reaction with the surface silanol groups. Bonding of neutral, polar ligands generally requires the addition of a catalyst, such as toluene-4-sulfonic acid or triethylamine, in the presence of sufficient water to generate monolayer coverage of the silica. The presence of water speeds up the hydrolysis of the alkoxy groups of the adsorbed organosilane, which tends to react with surface silanol groups rather than polymerize in solution. It seems to be a general problem in the preparation of polar bonded phases that surface silanol groups are blocked by physically adsorbed organosilanes, giving rise to a lower bonded phase density after workup than the maximum theoretically predicted. The bonded phase density can be increased by repeating the reaction a second time or exposed silanol groups minimized by endcapping.

In one aspect of the present invention, the beads and other media of the invention are characterized by having low amounts of metal contaminants or other contaminants that can bind DNA. The preferred beads of the present invention are characterized by having been subjected to precautions during production, including a decontamination treatment, such as an acid wash treatment, designed to substantially eliminate any multivalent cation contaminants (e.g. Fe(III), Cr(III), or colloidal metal contaminants). Only very pure, non-metal containing materials should be used in the production of the beads in order that the resulting beads will have minimum metal content.

In addition to the beads themselves being substantially metal-free, Applicants have also found that, to achieve optimum peak separation during MIPC, the separation column and all process solutions held within the column or flowing through the column are preferably substantially free of multivalent cation contaminants. As described in commonly owned U.S. Pat. No. 5,772,889 to Gjerde (1998), and in co-pending U.S. patent applications Ser. No. 09/081,040 (filed May 18, 1998) and Ser. No. 09/080,547 (filed May 18, 1998) this can be achieved by supplying and feeding solutions that enter the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer.

There are two places where multivalent cation binding agents, e.g., chelators, are used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis,* Robert E. Krieger Publishing Co. (1964). In the present invention, a preferred multivalent cation binding agent is EDTA.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the polynucleic acid through a matched ion process so that the polynucleic acid can interact with the nonpolar surface of the separation media. The requirements for the extent of nonpolarity of the counterion-DNA pair depends on the polarity of the separation media, the solvent conditions required for separation, the particular size and type of fragment being separated. For example, if the polarity of the separation media is increased, then the polarity of the counterion agent may have to change to match the polarity of the surface and increase interaction of the counterion-DNA pair. Triethylammonium acetate is preferred although quaternary ammonium reagents such as tetrapropyl or tetrabutyl ammonium salts can be used when extra nonpolar character is needed or desired. In general, as the polarity of the alkyl group is increased, size specific separations, sequence independent separations become more possible. Quaternary counterion reagents are not volatile, making collection of fragments more difficult.

In some cases, it may be desired to increase the range of concentration of organic solvent used to perform the separation. For example, increasing the alkyl length on the counterion agent will increase the nonpolarity of the counterion-DNA pair resulting in the need to either increase the concentration of the mobile phase organic solvent, or increase the strength of the organic solvent type, e.g. acetonitrile is about two times more effective than methanol for eluting polynucleic acids. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkylammonium salts. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography, 2nd Ed.,* Dr. Alfred H üthig Verlag Heidelberg (1987). Counterion agents that are volatile are preferred for use in the method of the invention, with triethylammonium acetate (TEAA) and triethylammonium hexafluoroisopropyl alcohol being most preferred.

Applicants have found that the temperature at which the separation is performed affects the choice of organic solvents used in the separation. One reason is that the solvents affect the temperature at which a double stranded DNA will melt to form two single strands or a partially melted complex of single and double stranded DNA. Some solvents can stabilize the melted structure better than other solvents. The other reason a solvent is important is because it affects the distribution of the DNA between the mobile phase and the stationary phase. Acetonitrile and 1-propanol are preferred solvents in these cases. Finally, the toxicity (and cost) of the solvent can be important. In this case, methanol is preferred over acetonitrile and 1-propanol is preferred over methanol.

When the separation is performed at a temperature within the above range, an organic solvent that is water soluble is preferably used, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Solvents which are particularly preferred for use in the method of this invention include methanol, ethanol, 2-propanol, 1-propanol, tetrahydrofuran (THF), and acetonitrile, with acetonitrile being most preferred overall.

In an important aspect of the present invention, Applicants have developed a standardized criteria to evaluate the performance of a DMIPC separation media. DMIPC as used herein, is defined as a process for separating heteroduplexes and homoduplexes using a non-polar separation medium (e.g., beads or rod) in the column, wherein the process uses a counterion agent, and an organic solvent to desorb the nucleic acid from the medium, and wherein the medium is characterized as having a Mutation Separation Factor (MSF) of at least 0.1. In one embodiment, the medium has a Mutation Separation Factor of at least 0.2. In a preferred embodiment, the medium has a Mutation Separation Factor of at least 0.5. In an optimal embodiment, the medium has a Mutation Separation Factor of at least 1.0.

The Mutation Separation Factor (MSF) is determined by the following equation:

$$MSF=(\text{area peak 2}-\text{area peak 1})/\text{area peak 1}$$

where area peak 1 is the area of the peak measured after DMIPC analysis of wild type and area peak 2 is the total area of the peak or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

An important aspect of the present invention concerns a method for altering the chromatographic mobility of DNA fragments by covalent attachment of a non-polar tag. In one embodiment, PCR primers are tagged (e.g., at the 5' end) with a non-polar group and contacted with a complimentary template for PCR amplification. The resulting amplified DNA fragment will then contain a non-polar tag at one terminus or the other, if one primer is tagged. If both primers are tagged, the amplified DNA fragment will contain non-polar tags at each of its ends.

As defined herein, a "chemical tag" is a molecule which can be covalently bound to a polynucleotide for the purpose of increasing the sensitivity of detection of the polynucleotide (e.g., a label) and/or increasing the retention time of the polynucleotide during separation by MIPC.

A "tagged polynucleotide" is a polynucleotide which has been modified by covalent attachment of a chemical tag. The location of the chemical tag can occur at either end of a polynucleotide fragment or at an intermediate location. Multiple tags can be attached. However, in a preferred embodiment, a single molecule of chemical tag is attached to a polynucleotide. In a most preferred embodiment, the tag is attached to the 5'end.

An example of the preparation of a tagged polynucleotide includes the use of a PCR primer having a covalently attached fluorescent chemical tag at the 5' end. Such a primer can be used in a PCR amplification to incorporate the chemical tag into dsDNA.

In a particular aspect, the invention is a method for increasing the retention time of a polynucleotide analyzed by Matched Ion Polynucleotide Chromatography by binding a non-polar tag to a polynucleotide. Examples of suitable non-polar tags include a hydrocarbon group such as alkyl, cycloalkyl, aryl and arylalkyl groups. Preferably, the tagged polynucleotide/counterion complex is essentially completely soluble in the mobile phase at all concentrations of organic solvent used in the mobile phase during the MIPC separation of the polynucleotide. The term "alkyl" describes straight or branched hydrocarbon radical chains of 1 to 8 carbons atoms and preferably 1 to 24 carbon atoms. Examples of these alkyl groups include, but are not limited to methyl, ethyl, propyl, iso-propyl, butyl, tert-butyl, pentyl, and hexyl. The terms "aryl" and "arylalkyl" describe aromatic radical groups and can include monocyclic, bicyclic, and tricyclic aromatic hydrocarbon groups. Example of these aromatic groups, include, but are not limited to phenyl, naphthyl, and pyrenyl. The hydrocarbon group can also be substituted with various functional groups such as aldehyde, ketone, ester, ether, alkyl, alkoxy, halogen (e.g., Cl, F, Br, or I), haloalkyl, polyhaloalkyl, hydroxy, cyano, and nitro.

Preferred tagging groups include FAM, JOE, TAMRA, and ROX (Operon Technologies, Inc., Alameda, Calif.). These groups can be covalently attached to a desired primer by reaction with a 5'-amino-modified oligonucleotide in the presence of sodium bicarbonate and dimethylformamide, as described in detail in Example 1. Alternatively, covalently tagged primers can be obtained commercially (e.g., from Midland Certified Reagent, Co.). Fluorescent dyes are available form Molecular Probes, Inc. (Eugene, Oreg.) and Amersham Life Science. Inc. (Cleveland, Ohio).

MIPC separates DNA fragments based on base pair length. In general, longer DNA fragments have a longer retention time on a MIPC column than shorter fragments. DNA fragments containing non-polar tags have increased retention times compared to their corresponding untagged fragments. This characteristic of MIPC separation media is used by Applicants to improve the separation of two closely running DNA fragments. In one embodiment of the invention, one fragment is PCR amplified with a non-polar tagged primer and the other is amplified with an untagged primer. In another aspect, the invention is a method for enhancing the detection of a polynucleotide analyzed by MIPC by binding a detectable tag to a polynucleotide. An example of such a tag is a fluorophore, i.e., a fluorescence emitting group (e.g., as described in U.S. Pat. No. 5,639,874 to Middendorf (1997) and U.S. Pat. No. 5,800,996 to Lee (1998), each of which is incorporated by reference herein). The introduction of fluorescent tags into DNA fragments to enhance detection sensitivity is known in the gel electrophoresis DNA separation art. However, as discussed above, the many deficiencies associated with gel based DNA separations make this method poorly suited for DNA separations wherein high throughput and automation of the analysis is important.

The use of fluorescent tags to enhance the detection of DNA fragments separated by liquid chromatography has been described in the following references which are incorporated in their entireties herein: Oefner, et al. *Research Reports* 16:898 (1994) and Oefner, et al., *Anal. Biochem.*, 223:1 (1994). Morgan, et al., (*J. Chromatography* 536:84 (1991)) found that fluoroscein and biotin tagged DNA fragments could not be completely eluted from a porous alkylated polystyrene HPLC column. Changing the column packing to other porous polymers improved the elution behavior of the tagged DNA, but not their resolution. Further advances were made by Oefner and co-workers in the use of fluorescent labels to enhance the detection sensitivity in oligonucleotides and double stranded DNA separations by HPLC on non-polar stationary phases. Oefner, et al., (*Analytical Biochemistry* 223:1 (1994)) describe the use of fluorescent dyes to covalently label double stranded nucleic acids which were separated by HPLC. They report an increase in sensitivity of 167–1000-fold compared to uv absorbance detection. However, their separation system did not include precautions against contamination of the media or chromatographic system by multivalent cations, which precautions have been shown by Applicants to essentially eliminate the degradation in separation performance.

Figure 13:
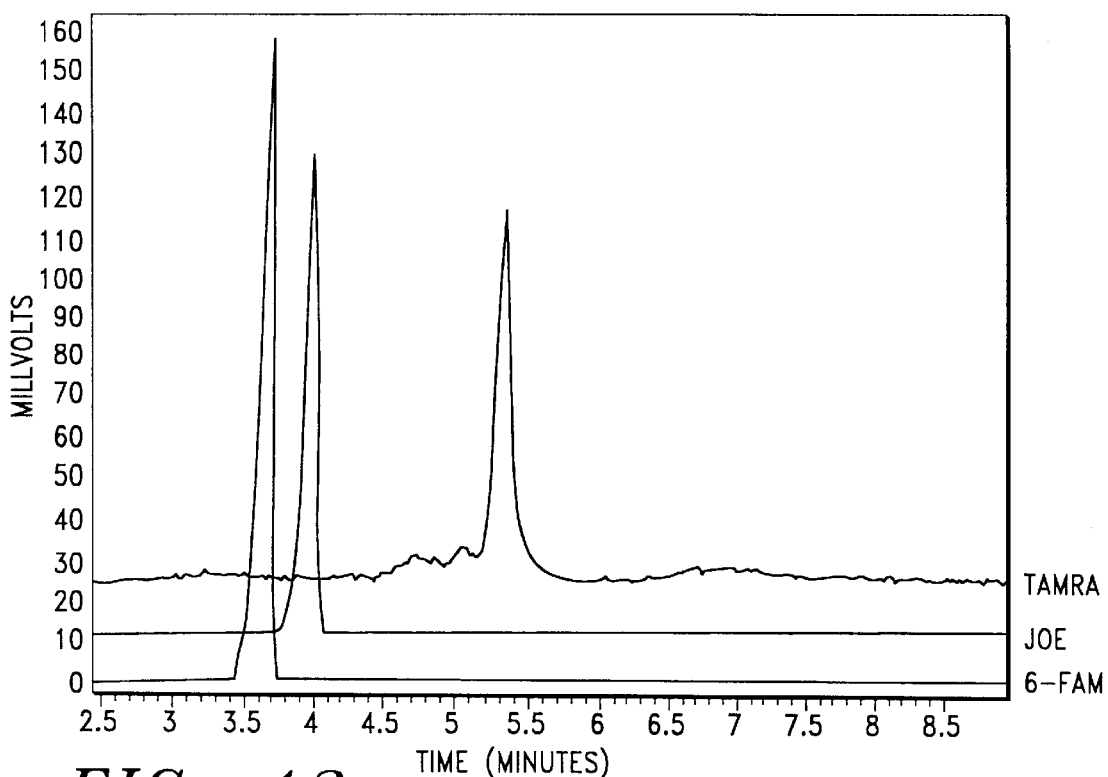
FIG. 13 shows the effect on the retention time in an MIPC chromatogram on DNA fragments prepared by PCR using three primers, each tagged with a different non-polar fluorescent group.

In another embodiment of the present invention, MIPC is used to separate mixtures of DNA fragments wherein one or more DNA components of the mixture are tagged with one or more fluorescent dye in order to enhance the sensitivity of detection of the fragments. In addition to enhancing the sensitivity of detection, the non-polar nature of fluorescent dyes can also have beneficial effects on the separation characteristics of the chromatography by favorably altering the retention time of tagged fragments, as discussed hereinabove. The retention time of an "A" allele tagged with three different non-polar fluorescent tags, TAMRA, JOE, and FAM, is shown in FIG. 13. The "A" allele is a 209 bp fragment from the human Y chromosome, locus DYS271, with an A to G mutation at position 168. The retention time of the untagged "A" allele was 3.2 minutes. As can be seen, the retention times of the tagged species was increased from about 0.3 minutes to 2.1 minutes. The result is a much improved separation.

In one embodiment of the invention, the fluorescent dyes can be covalently bonded to the DNA fragments. In another embodiment, the dyes can be bound by reversible interactions (such as by intercalation or by binding into a DNA groove). In either case the fluorescent dye greatly enhances the sensitivity of detection of the DNA fragment compared to uv detection. The use of fluorescent dyes to enhance the detection sensitivity of DNA fragments separated by MIPC or DMIPC has not been previously disclosed. Fluorescent tags provide a label for detection (this will be discussed hereinbelow) and enhance detection relative to uv. Thus, they are very useful when limited amounts of sample are available for analysis. The only requirement for tagging DNA with intercalating fluorescent dyes is that the intercalated complex be stable under MIPC and DMIPC conditions, i.e., between about 50° C. and 70° C., preferably, between 50° C. and 60° C.

In a particular embodiment, a covalently bound fluorescent tag is introduced into a DNA fragment during PCR amplification. One or both primers can be tagged with desired fluorescent dyes as described in Example 1. The primers are annealed to a complimentary portion of a target template and are extended by a DNA polymerase. Multiple iterations of the this process furnish an amplified product fragment which contains a fluorescent tag at one or both ends. Non-limiting examples of fluorescent dyes include 5-carboxyfluorescein (FAM), 2',7'-dimethoxy-4',5'-dichloro-6-carboxyfluorescein (JOE), N,N,N',N'-tetramethyl-6-carboxyrhodamine (TAMRA), and 6-carboxy-X-rhodamine (ROX), Fluorescein, Rhodamine, BODIPY-TR-X, Cascade Blue, and Alexa 350. The increase in the detection limit of DNA tagged with covalently bound fluorescent dyes is about 167 to 1000 times greater than uv detection at 260 nm. Covalent fluorescent tags have not been previously used to increase the sensitivity of detection of DNA fragments in MIPC/DMIPC separations.

In another aspect of the invention, reversible DNA-binding dyes are used to enhance the detection of double stranded DNA. The term "reversible DNA-binding dye" is used herein to include DNA intercalator dyes and DNA groove binding dyes. As defined herein, a "DNA intercalator dye" is a generally planar, aromatic, ring-shaped chromophore molecule which binds to DNA in a reversible, non-covalent fashion, by insertion between the base pairs of the double helix. The term "DNA groove binding dye" is defined herein to mean those chromophore molecules which reversibly bind by direct interaction with the edges of base pairs in either of the grooves (major or minor) of nucleic acids. These dyes are included in the group comprising non-intercalative DNA binding agents. Non-limiting examples of DNA groove binding dyes include Netropsin (N'-(2-amidinoethyl)-4-(2-guanidinoacetamido)-1,1'-dimethyl-N,4'-bi[pyrrole-2-carboxamide]) (Sigma), Hoechst dye no. 33258 (Bisbenzimide, B-2261, Sigma), Hoechst dye no. 33342, (Bisbenzimide, B2261, Sigma), and Hoechst dye no. 2495 (Benzoxanthene yellow, B-9761, Sigma). Preferred reversible DNA-binding dyes in the present invention include fluorescent dyes. Non-limiting examples of reversible DNA-binding dyes include PICO GREEN (P-7581, Molecular Probes), ethidium bromide (E-8751, Sigma), propidium iodide (P-4170, Sigma), Acridine orange (A-6014, Sigma), 7-aminoactinomycin D (A-1310, Molecular Probes), cyanine dyes (e.g., TOTO, YOYO, BOBO, and POPO), SYTO, SYBR Green I, SYBR Green II, SYBR DX, OliGreen, CyQuant GR, SYTOX Green, SYTO9, SYTO10, SYTO17, SYBR14, FUN-1, DEAD Red, Hexidium Iodide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, and LDS 751. Numerous reversible DNA-binding dyes are described in *Handbook of Fluorescent Probes and Research Chemicals,* Ch. 8.1 (1997) (Molecular Probes, Inc.); European Patent Application No. EP 0 634 640 A1; Canadian Patent No. CA 2,119,126; and in the following U.S. Pat. Nos. 5,410,030; 5,321,130; 5,432,134; 5,445,946; 4,716,905 (which publications are incorporated by reference herein).

In one embodiment, a polynucleotide sample is stained with a reversible DNA-binding dye, such as a fluorescent intercalating dye, prior to analysis. A preferred ratio of dye to DNA is about 1 molecule of dye per 30 base pairs. In another embodiment, a reversible DNA-binding dye is included in the chromatographic mobile phase. Advantageously, many such dyes (e.g., TOTO) have little or no intrinsic fluorescence and actually exhibit fluorescence only when intercalated into a polynucleotide.

Intercalating fluorescent dyes are very useful in enhancing detection of DNA mixtures by MIPC at 52° C. This is demonstrated dramatically in FIGS. 1 and 2. FIG. 2 shows MIPC separation chromatograms of a pUC18 HaeIII digest before and after staining with PICO GREEN. Trace "a" represents the separated mixture detected by uv at 260 nm before staining. Trace "b" represents the separated mixture detected by fluorescence after staining. The increase in the sharpness and resolution of the peaks in the fluorescence spectrum is clearly observable. A gradient mobile phase comprising solvent A (0.1M TEAA) and solvent B (25% acetonitrile in 0.1M TEAA) was used to elute the column. Solvent B was ramped up from 35% to 55% in three minutes, then from 55% to 65% in the next seven minutes. The concentration of solvent B was then held at 65% for 2 minutes, and ramped up to 100% over the next minute to wash the column, then equilibrated for the next injection by ramping down to 35% B over the next 1.5 minutes. The flow rate was 0.75 mL/min. The uv signal was monitored at 260 nm. Fluorescence was detected at 520 nm (excitation wavelength, 480 nm).

Figure 3:
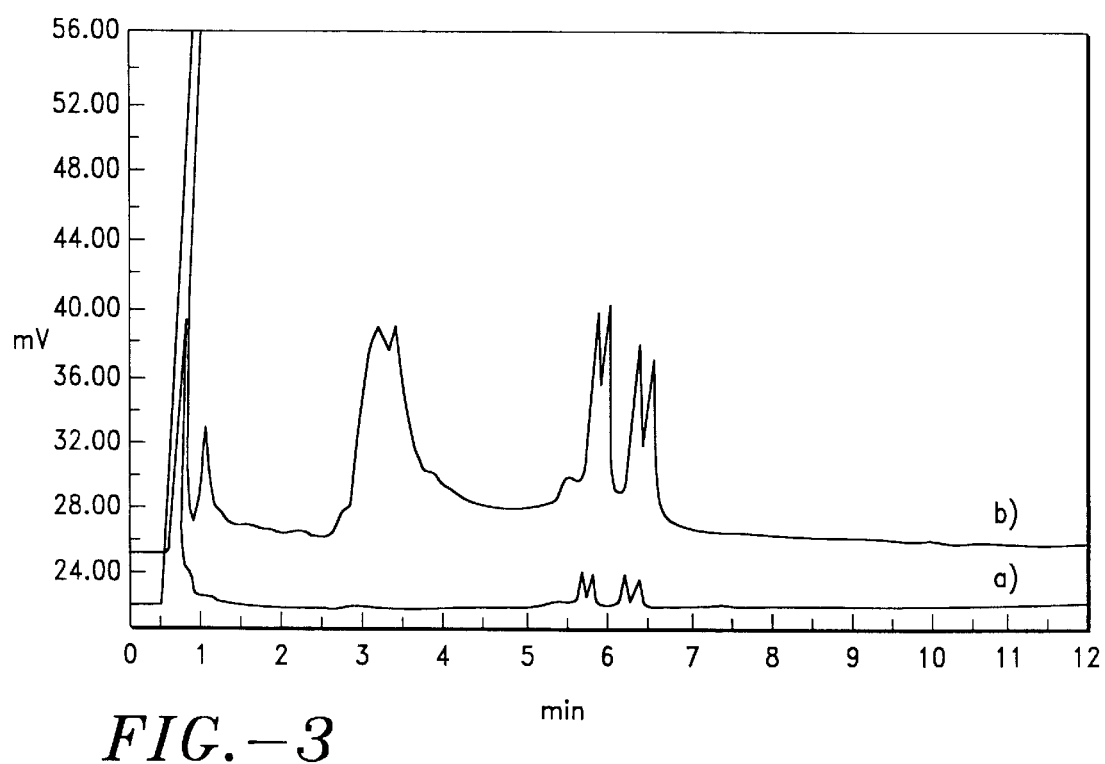
FIG. 3 is (a) a uv DMIPC chromatogram, and (a) a Hoechst 33258 fluorescent DMIPC chromatogram, of a homoduplex/heteroduplex separation.

FIG. 3 shows a similar comparison of uv to fluorescence detection in the separation of the mutation detection standard 209 bp mixture containing two homoduplexes and two heteroduplexes. Trace "a" shows the two pairs of well resolved, albeit small peaks, each pair representing the homoduplexes and the heteroduplexes. Trace "b" shows the separation of this same mixture when the mixture was stained with Hoechst 33258 (Sigma, Corp., St. Louis, Mo.) prior to MIPC. The chromatography was conducted in an identical manner as described above for FIG. 2, except that the fluorescence was monitored at 461 nm (excitation wavelength 350 nm). Again, there is an impressive increase in the size of these well resolved peaks. It is a surprising discovery by Applicants that in each of the above FIGS. 1 and 2, the retention time of the peaks was not altered by the intercalated dye. Detection of DNA fragments tagged with intercalated fluorescent dyes in these examples is up to about 10-fold greater than can be achieved with uv detection.

Although not preferred, radioactive elements can be used as chemical tags to increase the detection of DNA fragments in the present invention. Methods of incorporation of radioactive elements such as P-32 into DNA fragments are well known. Other examples of radioactive tags include S-35 and tritium. DNA fragments can be radioactively tagged, for example, by incorporation of radiolabeled bases during a PCR amplification or by other conventional methods (e.g., as described in U.S. Pat. No. 4,647,529 to Rodland (1989) and U.S. Pat. No. 5,656,742 to McCabe (1997)). Such tags may be required in analyses wherein the detection of exceptionally small amounts of DNA is required. Detection of the radioactive fragments preferably uses inline detection methods.

In an important aspect of the invention, mixtures of dsDNA tagged with different fluorescent dyes which are "uniquely detectable" from each other, can be used in "multiplex" applications to detect each component of a mixture independently of the other components of the mixture. The term "multiplex" is defined herein to mean the selective and simultaneous detection of each desired component of a mixture in the presence of all the other components of the mixture. The term "uniquely detectable" as used herein, means that the fluorescent emission (in the case of fluorophores) or absorbance (in the case of tags absorbing in the uv-vis spectrum) wavelength of each dye in a mixture is sufficiently distinct from every other dye so that every DNA fragment which is tagged with a different dye can be distinguished from any other tagged DNA fragment in the mixture. For example, the dyes Cascade Blue, FAM, JOE, TAMRA, and ROX, BODIPY-TR-X are uniquely detectable since their emission wavelengths are 430 nm, 522 nm, 550 nm, 580 nm, 605 nm, and 620 nm, respectively. As an example, these dyes can be used in a PCR system in which four different regions of a template are amplified simultaneously in the same container using four different primer sets. In this example, one of the primers for each template region to be amplified can be tagged with a particular fluorescent dye, wherein each tag attached to each primer is uniquely detectable from all the others. In this multiplex system, the four expected PCR products can be monitored simultaneously by chromatographing the mixture on a MIPC column and monitoring the separation at any of the wavelengths corresponding to the dyes used, i.e., 430 nm, 522 nm, 550 nm, 580 nm, 605 nm, and 602 nm. Multi-wavelength detectors are available commercially (e.g., HP 1100 Series fluorescence detector, Hewlett-Packard, Palo Alto, Calif.). Examples of the preparation of other fluorescent polynucleotides which can be used in a multiplex system is described in U.S. Pat. No. 4,855,225 to Fung (1989) and Nunnaly, et al., *Anal. Chem.* 69:2392 (1997) (which publications are each incorporated by reference in their entireties herein).

Examples of other tagging groups include chromophores which can be used in a multiplex system include compounds which absorb in the uv-vis spectrum at wavelengths which differ from the absorption wavelength of the nucleic acids. An example of such compounds are fluorescent tags, which in this aspect of the invention, are monitored by their distinctive uv-vis absorbance profiles, and not by their fluorescence emission properties. Further examples include porphyrin derivatives (e.g., texaphyrin) as described in U.S. Pat. No. 5,595,726 which is incorporated by reference herein.

Figure 14:
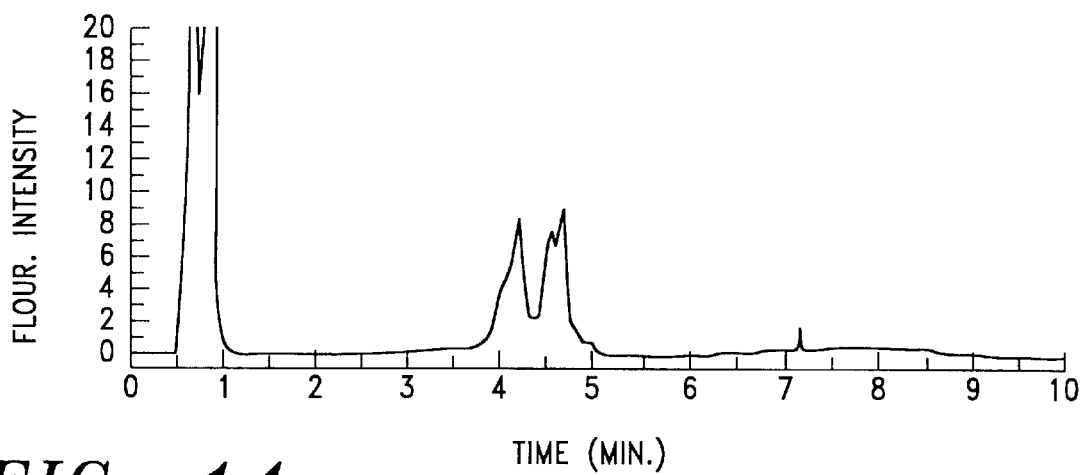
FIG. 14 shows a DMIPC chromatogram of a 209 bp mutation standard tagged with FAM and monitored at 520 nm.
Figure 15:
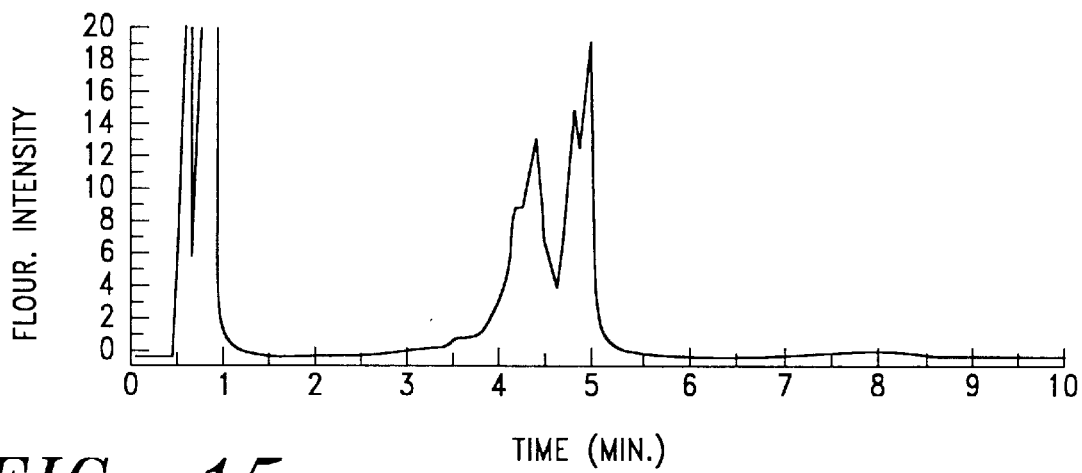
FIG. 15 shows a DMIPC chromatogram of a 209 bp mutation standard tagged with JOE and monitored at 548 nm.
Figure 16:
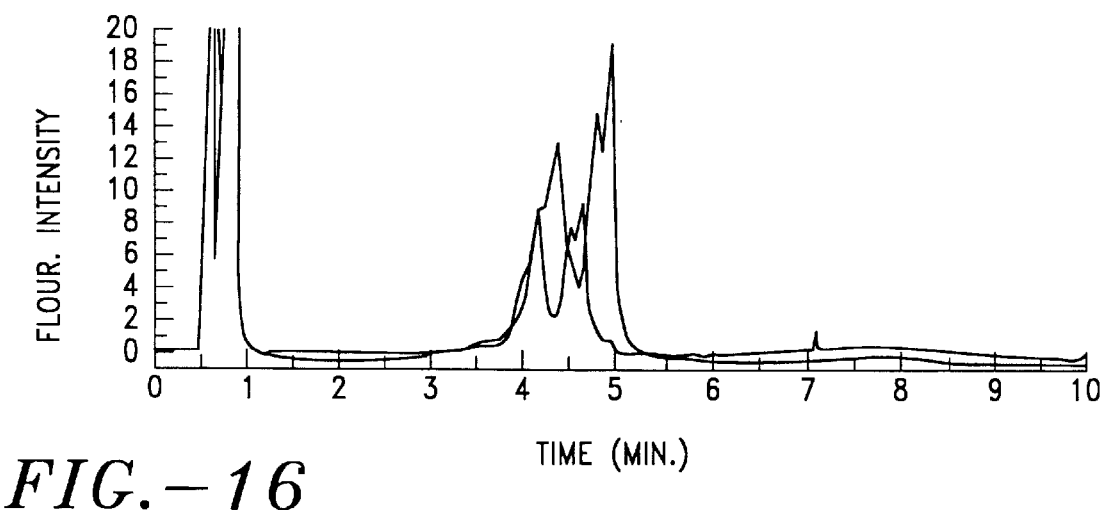
FIG. 16 shows a multiplex DMIPC chromatogram of a 209 bp mutation standard tagged with FAM and JOE.

FIGS. 14, 15, and 16 illustrate a multiplex DMIPC analysis of a 209 bp mutation standard tagged with FAM (520 nm) and JOE (548 nm). The pooled samples were analyzed on an MIPC column under partially denaturing conditions, 56° C., and the chromatography was monitored at 520 nm and 548 nm simultaneously. The chromatogram shown in FIG. 14 was monitored at 520 nm (exited at 496 nm). The chromatogram in FIG. 15 was monitored at 548 nm (exited at 520 nm). The chromatogram in FIG. 16 shows the chromatograms from FIGS. 14 and 15 superimposed for comparison. As can be seen in FIG. 16, the two samples are clearly distinguishable. For example, at 5 minutes retention time, the JOE tagged standard shows a strong peak while the FAM tagged standard shows essentially no response. At about 4.6 minutes retention time, the FAM tagged standard shows a peak while the JOE tagged standard shows a trough.

In another example, a number of uniquely detectable dyes can each be bound separately to a member of a primer set to generate a series of primers differing only in the identity of the bound dye. Each primer set in this series is used in a separate assay to amplify the same region of a template to produce a series of PCR amplified samples each having a uniquely detectable tag.

These samples can be mixed and screened simultaneously using MIPC, thereby greatly reducing analysis time and increasing throughput in screening assays. Primers tagged with fluorescent dyes can be obtained from Microsynth Corp., (Windisch, Switzerland).

A more detailed discussion of multiplex analysis can be found in Nunnally, et. al., *Anal. Chem.* 69:2392 (1997) and He, et. al., *Anal. Chem.* 70:3413 (1998). These references and the references contained therein are hereby incorporated by reference in their entireties herein.

In another embodiment of the invention, DNA fragments covalently tagged with a non-polar group can be used to improve the sensitivity and accuracy of mutation detection. In this embodiment, a DNA sample containing a putative mutation is hybridized with corresponding wild type. Hybridization, a standard technique in the DNA art, is effected by heating a mixture of sample and wild type to about 90° C. for about 5 minutes and then slowly cooling the mixture to ambient temperature over about 45 to 60 minutes. During the heating period, all the double stranded DNA in the mixture denatures to single strands. Upon cooling, the complimentary strands in the mixture recombine. If the sample contains a mutation, the hybridized mixture will contain two homoduplexes and two heteroduplexes resulting from the recombination of all the possible combinations of complimentary strands present in the mixture. An example of the hybridization process is shown schematically in FIG. 4.

By selecting which specific strand of the wild type and/or sample to tag with a non-polar group, greater specificity and accuracy can be obtained in detecting the presence or absence of a mutation. Importantly, as will be seen in the discussion hereinbelow, by selectively tagging a specific strand, the presence or absence of a mutation can be confirmed under conditions which would normally preclude such confirmation.

The symbols which will be used in the discussion and Figures hereinbelow, and their meaning, are listed below for reference:

T=tag
W=wild type single strand
W'=complimentary wild type sequence
M=mutant single strand
M'=complimentary mutant sequence PCR product prepared separately is represented in bold font. A bracket, "[ . . . ]" indicates that the bracketed fragment my be present in trace amounts or not at all.

Applicants have found that DNA fragments which are tagged with non-polar groups are retained longer on an MIPC column, whether the chromatography is done under non-denaturing conditions or under partially denaturing conditions. In an important aspect of the invention, this observation is used to advantage in order to detect mutations using fluorescent tagged DNA. In a preferred embodiment, the fluorescent tags are also non-polar; DNA fragments so tagged will have a longer retention time on an MIPC column than an untagged fragment of the same base pair length. By designing a system in which a specific strand of a specific duplex is tagged, the detection of mutations in a sample can be optimized. This optimization is accomplished by altering the retention time of a fragment by means of a non-polar tag in order to improve its separation from close running fragments. Optimization by the use of non-polar fluorescent tags is also manifested in enhanced detection of the fluorescent moiety compared to uv detection of an untagged fragment.

Referring to the symbols identified hereinabove, one such embodiment is shown in FIG. 5. A wild type fragment is amplified by PCR using fluorescent tagged complimentary primer to furnish the fluorescent tagged wild type fragment W W'-T. Upon hybridization with a sample containing a putative mutant strand, M M', a mixture of homoduplexes and heteroduplexes is obtained, as depicted on the right side of the "equals" sign. The spacing of the fragments on the right side of the "equals" sign shows their relative retention times on a MIPC column under DMIPC conditions. The fragments M W'-T and W W'-T have the longest retention times because they carry a non-polar tag. They are well resolved from the untagged fragments. More to the point, the chromatogram is simplified, since only the peaks representing the fluorescent tagged fragments are seen by a fluorescence detector. M W'-T and W W'-T are separated from each other since the chromatography is performed under partially denaturing conditions. If the sample did not contain a mutation, but only wild type (FIG. 6), then only a single fluorescent peak would be seen since only a single, relatively long retention time tagged fragment would be present, i.e., W W'-T.

Another embodiment is shown in FIG. 7, wherein the tagged wild type, W W'-T is present in small amount relative to a sample containing mutant DNA. In this case, all the tagged wild type would be consumed in the hybridization with excess mutant fragment. The species shown in brackets would therefore be undetectable. If no mutation were present (FIG. 8), a single fluorescent peak would be seen at the retention time of the tagged wild type homoduplex. However, if a mutation were present (FIG. 7), a single fluorescent peak due to the heteroduplex, M W'-T, representing the mutation would be well separated from the other fragments in the mixture by virtue of its long retention time due its non-polar tag.

Another embodiment of the invention is shown schematically in FIG. 9. In this case, a sample tagged in the complimentary strand is hybridized with a large excess of separately amplified wild type fragment in order to ensure complete hybridization of the sample. Excess wild type will not interfere in the analysis because it is not tagged and will therefore not be seen by a fluorescence detector. If the sample contains a mutation, the heteroduplex would be easily detected as having the longest retention time and being the only fluorescent species in the mixture. It will be noted that the tagged sample is not present in the hybridized mixture since excess wild type drives the hybridization to completion, converting all the tagged sample to heteroduplex. An important and novel advantage of this embodiment is that the wild type need not be added in stoichiometric amount relative to sample in the hybridization process. Prior to the present invention, when using liquid chromatographic methods in mutation detection, it was been necessary to determine the amount of sample present after PCR amplification so that a stoichiometrically equivalent amount of wild type could be added to the sample prior to hybridization. This was important because addition of an excess of wild type could interfere in the mutation detection analysis by possibly obscuring the presence of a putative mutation. The method of the present invention eliminates the need to quantitate the amount of sample following PCR amplification and saves both time and expense. In fact, as demonstrated in the examples hereinabove and in FIG. 9, deliberate addition of an excess of wild type (e.g., 10–1000-fold excess) prior to hybridization can result in a simplified chromatogram and eliminate ambiguity regarding the presence or absence of a mutation. Ambiguity is further avoided by withholding one half of the tagged moiety and hybridizing the other half with the untagged component. Following hybridization, the unhybridized tagged component which was withheld is added back to the hybridized mixture and analyzed by MIPC. The unhybridized tagged component serves as an internal tagged standard. Thus, in FIG. 6, for example, if the entire tagged moiety (present in excess) was hybridized with the sample, only one predominant tagged peak would be seen because the excess W W'-T would drive the reaction to consume all the M M'. It might not be clear, therefore, if the tagged product was W W'-T or M W'-T. By adding back one half of the unhybridized W W'-T, a tagged internal standard is introduced. Now, if two tagged peaks are seen in the MIPC chromatogram, the sample contained a mutation. If a single tagged peak is seen in the MIPC chromatogram, then the sample did not contain a mutation. Methodology which enables the detection of mutations without quantitation of the sample prior to hybridization has not been heretofore reported. This approach saves a significant amount of time in the analysis of samples containing putative mutations.

FIG. 10 shows wild type and sample tagged with the same fluorescent tag. In this case, the presence of a mutation is easily detected since the doubly tagged heteroduplex would have a significantly longer retention time than singly tagged or untagged fragments. If the sample did not contain a mutation, a doubly tagged homoduplex would be formed. This would have the longest possible retention time and be the only tagged fragment in the mixture.

FIG. 11 shows a single strand of wild type and mutant tagged with different fluorescent tags. In this case fragments can be monitored in a multiplex fashion by monitoring the chromatography at the T and T' emission wave lengths.

FIG. 12 shows four different fluorescent tags, one on each strand of the sample and the wild type. Multiplex analysis of the hybridized mixture is possible by monitoring the chromatography at each specific wave length corresponding to each respective tag.

In a related embodiment, the selectively bound non-polar tags, described hereinabove, are hydrocarbons which are not fluorophores. Such non-polar tags will alter retention times, as described hereinabove, and provide much improved DMIPC separations of heteroduplex and homoduplex mixtures. Examples of suitable non-polar tags include a hydrocarbon group such as alkyl, cycloalkyl, aryl and arylalkyl groups. Preferably, the tagged polynucleotide/counterion complex is essentially completely soluble at all concentrations of organic solvent used in the mobile phase during the MIPC separation of the polynucleotide. The term "alkyl" describes straight or branched hydrocarbon radical chains of 1 to 8 carbons atoms and preferably 1 to 24 carbon atoms. Examples of these alkyl groups include, but are not limited to methyl, ethyl, propyl, iso-propyl, butyl, tert-butyl, pentyl, and hexyl. The terms "aryl" and "arylalkyl" describe aromatic radical groups and can include monocyclic, bicyclic, and tricyclic aromatic hydrocarbon groups. Examples of these aromatic groups, include, but are not limited to phenyl, naphthyl, and pyrenyl. The hydrocarbon group can also be substituted with various functional groups such as aldehyde, ketone, ester, ether, alkyl, alkoxy, halogen (e.g., Cl, F, Br, or I), haloalkyl, polyhaloalkyl, hydroxy, cyano, and nitro. All of the embodiments of using chemical tags in mutation detection described hereinabove can be applied to advantage with the use of non-polar tags.

Depending on the specific separation problem related to mutation detection by DMIPC, a non-polar tag can be attached to any of the other possible primers to achieve, not only the improved separations shown in the schematic representations, but also the greatly improved detection sensitivity afforded by the fluorescent tags.

Another aspect of the present invention provides a method for increasing the melting temperature of a domain of dsDNA. Mutations cannot be detected in fragments which have a low melting terminal domain relative to the domain containing a mutation, because the temperature required to partially denature the mismatched base pair, is higher than the melting temperature of the terminal domain. Therefore, the entire double strand would denature. In the prior art, in order to prevent complete denaturation, a high melting terminal domain is created by PCR amplification using primers which contain, e.g., a series of high melting G-C bases. These bases are incorporated into the terminal portion of the desired fragment and prevent the fragment from completely denaturing at the temperature required to detect a mutation. Applicants have surprisingly found that non-polar chemical tags on DNA fragments, introduced by the use of covalently tagged primers in PCR amplifications, can be used in a completely novel method of clamping a low melting terminal portion of a DNA heteroduplex which contains a mutation in a higher melting domain. This method, called "column clamping" herein, avoids the expensive and labor intensive use of G-C clamps. Without wishing to be bound by theory, Applicants believe that a terminal non-polar tag increases the interaction of the terminal portion of a DNA fragment with the stationary phase. This increased interaction draws the adjacent terminal region of the fragment closer to the stationary phase through its interaction with the counter ion. The double stranded nature of the terminal domain is thereby stabilized. The increased stability of the terminal domain double strand manifests itself in a higher melting temperature.

Figure 18:
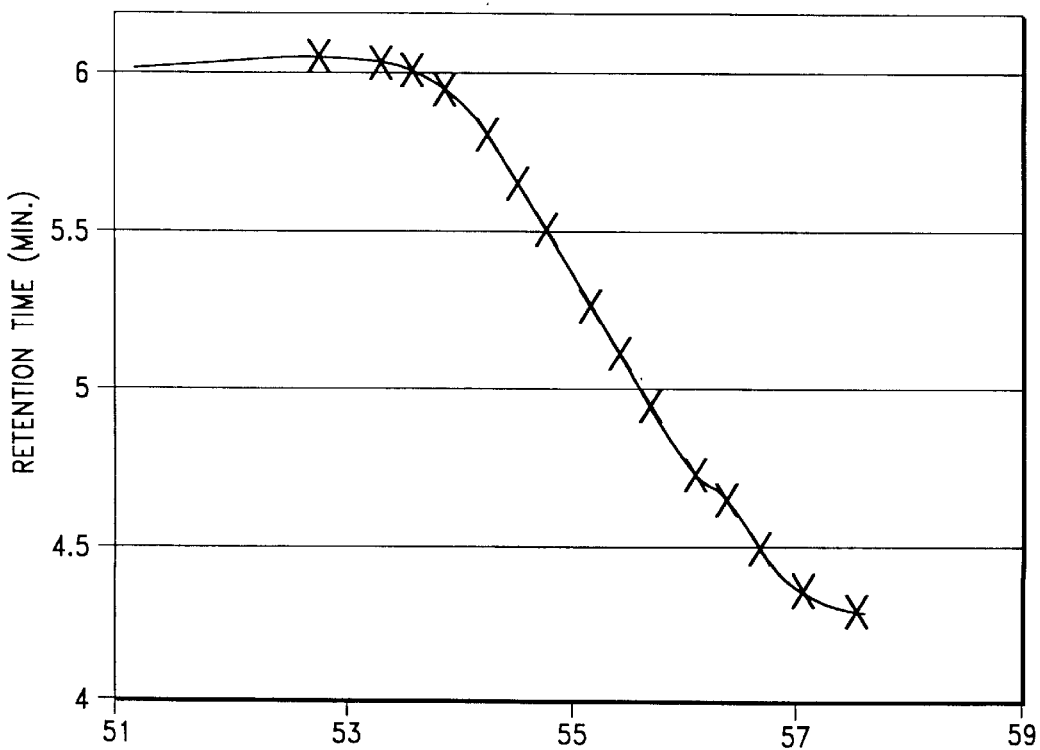
FIG. 18 shows a "melting curve" of a 209 bp DNA fragment determined by MIPC.
Figure 17:
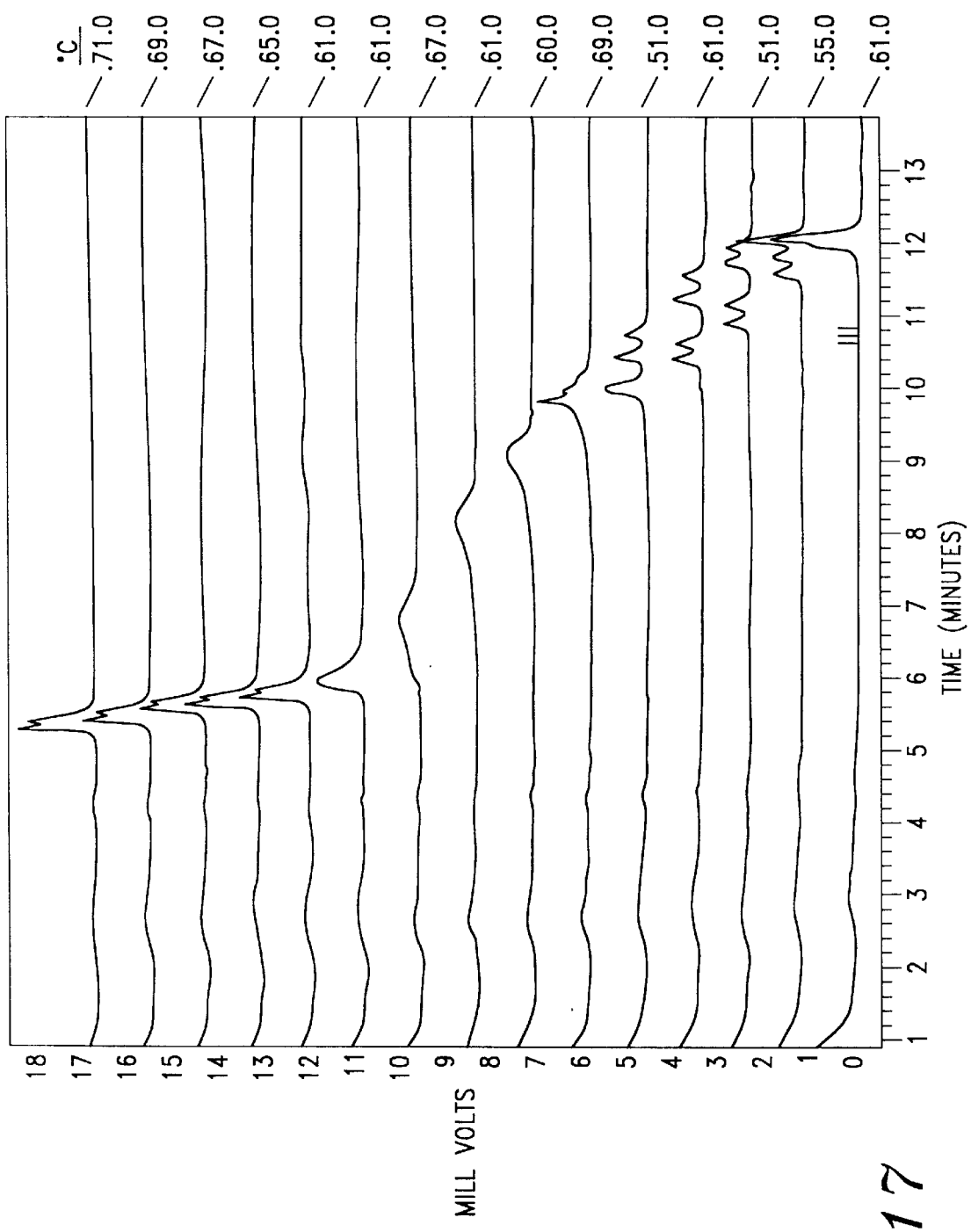
FIG. 17 shows a comparison of MIPC chromatograms of a 209 bp dsDNA fragment performed at a series of temperatures.

The term "temperature titration" of as used herein is an experimental procedure in which the retention-time of a dsDNA fragment separated by MIPC is plotted (e.g., as the ordinate) against column temperature (e.g., as the abscissa). This is demonstrated experimentally by plotting the retention time of a DNA fragment against the temperature at which the chromatography is performed as described in Example 4 and shown in FIG. 17. The retention time decreases with increasing temperature, the fully denatured fragments having the shortest retention time. The inflection point of the temperature vs. retention time curve is the "melting temperature", defined in the art to mean the temperature at which 50% of the DNA fragment population is denatured and in equilibrium with the duplex form. FIG. 18 shows the change in retention time of a DNA fragment with increasing temperature. As the temperature at which the duplex is fully denatured into single strands, the originally resolved peaks collapse into a doublet representing single stranded polynucleotides.

Many non-polar tags can be used for the purpose of effecting column clamping. Examples of suitable non-polar tags include a hydrocarbon group such as alkyl, cycloalkyl, aryl and arylalkyl groups. Preferably, the tagged polynucleotide/counterion complex is essentially completely soluble in the mobile phase at all concentrations of organic solvent used during the MIPC or DMIPC separation of the polynucleotide. The term "alkyl" describes straight or branched hydrocarbon radical chains of preferably 1 to 24 carbon and most preferably of 1 to 8 carbon atoms. Examples of these alkyl groups include, but are not limited to methyl, ethyl, propyl, iso-propyl, butyl, tert-butyl, pentyl, and hexyl. The terms "aryl" and "arylalkyl" describe aromatic radical groups and can include monocyclic, bicyclic, and tricyclic aromatic hydrocarbon groups. Examples of these aromatic groups, include, but are not limited to phenyl, naphthyl, and pyrenyl. The hydrocarbon group can also be substituted with various functional groups such as aldehyde, ketone, ester, ether, alkyl, alkoxy, halogen (e.g., Cl, F, Br, or I), haloalkyl, polyhaloalkyl, hydroxy, cyano, and nitro. As the hydrophobicity of a tag increases, a higher concentration of acetonitrile is required to elute the tagged DNA from the column. Thus, a tag can comprise any number of carbon atoms which can be eluted from a MIPC column with the organic solvent and counterion agent of the mobile phase.

A non-polar tag is attached to a primer as described in Example 1, followed by PCR amplification of a sample template to furnish a desired, terminally non-polar tagged, DNA fragment. Amplification of the same template with an untagged primer produces a DNA sample fragment having a lower melting terminal domain. To check for the presence of a mutation, the tagged fragment so produced is then hybridized with wild type. If the fragment contained a mutation then a pair of homoduplexes and a pair of heteroduplexes will be formed. Analysis of the hybridized mixture by DMIPC at about 56° will show the heteroduplexes, at a shorter retention time than, and well resolved from, the homoduplexes.

Other features of the invention will become apparent in the course of the following descriptions of exemplary embodiments which are given for illustration of the invention and are not intended to be limiting thereof.

Procedures described in the past tense in the examples below have been carried out in the laboratory. Procedures described in the present tense have not yet been carried out in the laboratory, and are constructively reduced to practice with the filing of this application.

EXAMPLES

Example 1

Synthesis of a Primer Covalently Tagged with a Non-polar Fluorescent Group

To a 1.4 mL centrifuge tube is added 5–15 nmoles of 5'-amino-modified oligonucleotide and ice cold nuclease free water, to bring the total volume to 35 $\mu$L. After warming to ambient temperature, 5 $\mu$L of sodium bicarbonate 10X buffer is added. To one vial of fluorescent dye (e.g., Fluorescein, Rhodamine, TAMRA, JOE, or 6-FAM) is added 50 $\mu$L dimethylformamide and the tube is vortexed to dissolve the dye. Then, 10 $\mu$L of the dye solution is immediately added to the oligonucleotide solution. The reaction mixture is vortexed and allowed to incubate at ambient temperature for 45 minutes.

Following incubation, 5 $\mu$L of the "precipitant", a precipitation enhancing material found in kits F1270 and F1290 and described in Technical Bulletin #TB200, Promega, Corp., Madison, Wis. (this reference is incorporated by reference herein in its entirety) and 450 $\mu$L of 95% ice cold ethanol are added to the reaction mixture. After gentle vortexing and centrifugation (12,000 rpm for 2 min. at 4° C.), a brightly colored pellet will be evident. The supernatant is carefully removed with a 100–200 $\mu$L pipeter and the pellet is washed with additional 400 $\mu$L aliquot of ice cold 70% ethanol until the washings are colorless. The fluorescent tagged nucleotide pellet obtained in this manner can be stored at −20° for about 6 months.

Example 2

The Effect of Non-polar Fluorescent Tags of MIPC Retention Time

A sample of DYS 81 "A" allele PCR product was fluorescently tagged by using TAMRA tagged forward primers in the PCR process. The DYS 81 "A" allele is the wild type of the DYS271 209 base pair fragment described in Kuklin et al., *Genetic Testing* 1:201 (1998) (this publication is incorporated herein by reference). Plasmid A (Part no. CSP1041, Teknova, Half Moon Bay, Calif.), containing the wild type human chromosome sY81, was amplified using a forward primer (Part no. 9218-003, Teknova) 5' tagged with TAMRA and having the following sequence: 5'-AGGCACTGGTCAGAATGAAG-3'. (The tagging was performed by Synthegen, Inc., Houston, Tex.) The reverse primer was 5'-AATGGAAAATACAGCTCCCC-3'. In a similar manner, DYS 81 "A" allele samples were tagged with JOE and 6-FAM.

Separate injections of 2 $\mu$L each were applied to a MIPC column. Each injection was eluted with the mobile phase gradient comprising solvent A (0.1M TEAA) and solvent B (25% acetonitrile in 0.1M TEAA).

| Time (min) | % A | % B |
|---|---|---|
| 0 | 48 | 52 |
| 0.5 | 45 | 55 |
| 4.0 | 38 | 62 |
| 5.5 | 0 | 100 |
| 6.5 | 48 | 52 |
| 8.5 | 48 | 52 |

The retention times of the above mentioned tagged DNA fragments are shown in FIG. 12.

Example 3

Multiplex Analysis of FAM and JOE Tagged DNA by DMIPC

Portions of the 6-FAM and JOE tagged DYS 81 "A" allele samples (Synthegen, Inc.) described in Example 2 were analyzed by DMIPC individually (as shown in FIGS. 14 and 15 respectively) and in a multiplex fashion (FIG. 16 using fluorescence detection (Hitachi Model L-7480 fluorescence detector). The excitation wave lengths for 6-FAM and JOE were 496 nm and 520 nm respectively. Monitoring was performed at 520 nm and 548 nm, the emission wave lengths for 6-FAM and JOE respectively.

The chromatography was performed under partially denaturing conditions, i.e. 56° C. in order to separate the homoduplex and heteroduplex mixture contained in the sample. The DMIPC conditions are the same for each sample as represented in FIGS. 14–16. Solvents A and B are identical to those described in Example 2, and the elution gradient is shown below:

| Time (min) | % A | % B |
|---|---|---|
| 0 | 50 | 50 |
| 0.5 | 47 | 53 |
| 4.0 | 40 | 60 |
| 5.5 | 0 | 100 |
| 6.5 | 50 | 50 |
| 8.5 | 50 | 50 |

Example 4

Effect of Temperature on the Retention Time in MIPC Separations of dsDNA

A 209 base pair fragment from the human Y chromosome locus DYS271 with an A to G mutation at position 168 was hybridized with wild type by heating to about 90° C. for 5 minutes then slowly cooling the mixture to ambient temperature over 45– to 60 minutes. A mixture of the wild type ("A" allele) mutant and ("G" allele) fragments is available as a Mutation Standard from Transgenomic, Inc., San Jose, Calif. The mutation is described by Seielstad et al., *Hum. Mol. Genet* 3:2159 (1994) (incorporated by reference herein). The hybridized sample was injected onto an MIPC column (50 mm×4.6 mm i.d.) at 51° C. The chromatography was monitored 260 nm using an UV detector. The heteroduplex present in the mixture was not denatured at 51° C.; therefore, a single peak was observed. The column was eluted at 0.9 mL/min with a solvent A: 0.1M TEAA and solvent B: 0.1M TEAA, 25% acetonitrile using the following gradient:

| T (min) | % A | % B |
|---|---|---|
| 0 | 67 | 33 |
| 0.1 | 62 | 38 |
| 12.1 | 40 | 60 |
| 12.2 | 0 | 100 |
| 12.7 | 0 | 100 |
| 12.8 | 67 | 33 |
| 15.3 | 67 | 33 |

The DMIPC retention times of the DYS271 209 bp hybridized mixture of heteroduplex and homoduplex species was measured as a function of oven temperature starting at 50° C. and continuing in 0.5 and 0.3 degree increments up to 57.5° C. (FIG. 17) in a temperature titration. The HPLC instrument was a unit controlled via RS232 interface from customized system software. The software control was from Transgenomic Inc. (San Jose, Calif.) custom prototype front-end software package (an extensively modified version of WAVEMaker™). This oven was produced from a Model PTC200 M.J. Research thermocycler that was modified to contain a DNASep™ column and preheat lines (150 cm×0.007"i.d.) made of PEEK tubing. The preheat tubing was interwound between the PCR tube wells (i.e., physically placed around the wells themselves and in thermal contact with the 96-well heating block) and then was connected to the column placed in a cavity machined out of the thermocycler. The oven response was high with approximately 10 seconds required to reach a set temperature. It took about 2 minutes for the fluid to reach the set temperature. This response was much faster than conventional ovens for liquid chromatography. The oven was peltier cooled, so that increases and decreases in temperature were reached rapidly.

A temperature titration was performed to generate a plot of retention time vs. temperature for a component (the first eluting heteroduplex) of the dsDNA mixture in this example (FIG. 18). The inflection point of this plot is the "melting temperature", i.e., the temperature at which the DNA in the mixture is in a 50:50 equilibrium between ds and single stranded form.

The TAMRA tagged forward primer prepared as in Example 1 is used with the untagged reverse primer in a PCR amplification to prepare a TAMRA tagged wild type homoduplex. This is mixed with the mutant homoduplex and hybridized. The retention time of the TAMRA (non-polar) tagged analog of the heteroduplex has a longer retention time on a MIPC column than the untagged sample. Chromatography on a MIPC column at a series of incrementally higher temperatures produces a series of chromatograms similar to FIG. 17 except that the retention times of the peaks in each chromatogram are shifted to longer retention time. In a similar manner, a plot of retention time vs. temperature produces a curve similar to FIG. 18 except that the entire curve is shifted to the right, i.e., to higher temperature. Therefore the melting temperature of a fragment having a non-polar tag is raised compared to that of the same untagged fragment. This example demonstrates the "column clamping" effect of non-polar tags.

EXAMPLE 5

Standard Procedure for Determining the DNA Separation Factor of Separation Media Separation particles are packed in an HPLC column and tested for their ability to separate a standard DNA mixture. The standard mixture is a pUC18 DNA-HaeIII digest (Sigma-Aldrich, D6293) which contains 11 fragments having 11, 18, 80, 102, 174, 257, 267, 298, 434, 458, and 587 base pairs, respectively. The standard is diluted with water and five $\mu$L, containing a total mass of DNA of 0.25 $\mu$g, is injected.

Depending on the packing volume and packing polarity, the procedure requires selection of the driving solvent concentration, pH, and temperature. The separation conditions are adjusted so that the retention time of the 257, 267 peaks is about 6 to 10 minutes. Any one of the following solvents can be used: methanol, ethanol, 2-propanol, 1-propanol, tetrahydrofuran (THF), or acetonitrile. A counter ion agent is selected from trialkylamine acetate, trialkylamine carbonate, trialkylamine phosphate, or any other type of cation that can form a matched ion with the polynucleotide anion.

Figure 19:
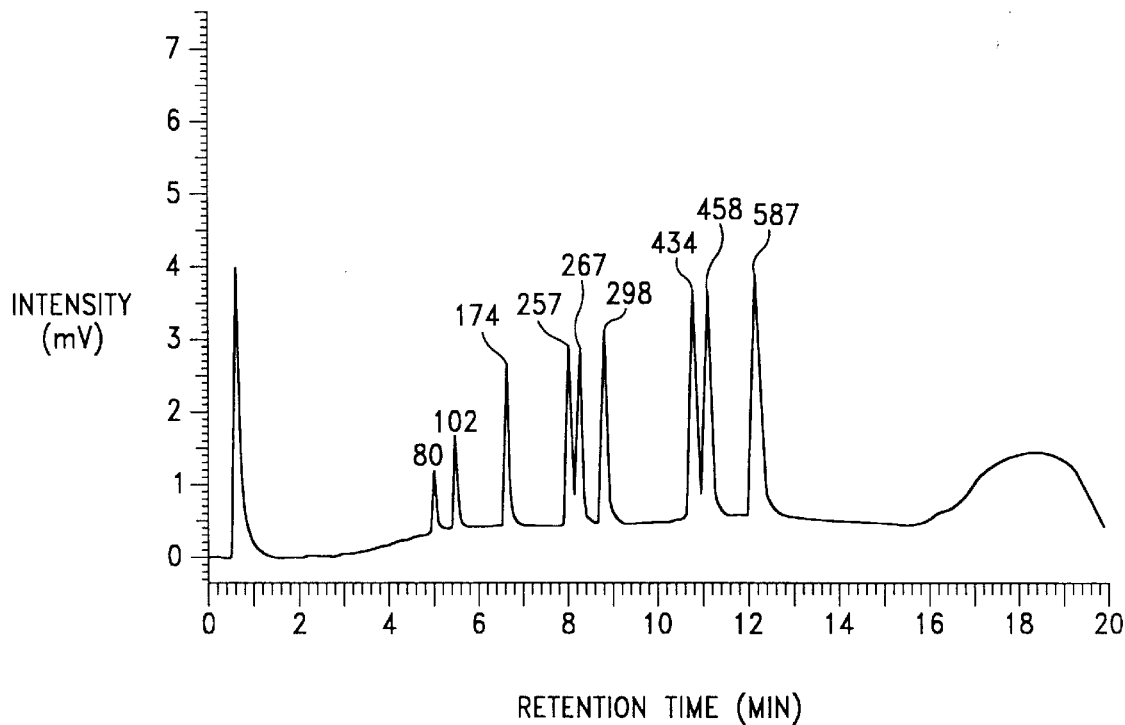
FIG. 19 is a MIPC separation of pUC18 DNA-HaeIII digestion fragments on a column containing alkylated poly (styrene-divinylbenzene) beads. Peaks are labeled with the number of base pairs of the eluted fragment.

As an example of this procedure, FIG. 19 shows the high resolution of the standard DNA mixture using octadecyl modified, nonporous poly(ethylvinylbenzene-divinylbenzene) beads. The separation was conducted under the following conditions: Eluent A: 0.1 M TEAA, pH 7.0; Eluent B: 0.1 M TEAA, 25% acetonitrile; Gradient:

| Time (min) | % A | % B |
|---|---|---|
| 0.0 | 65 | 35 |
| 3.0 | 45 | 55 |
| 10.0 | 35 | 65 |
| 13.0 | 35 | 65 |
| 14.0 | 0 | 100 |
| 15.5 | 0 | 100 |
| 16.5 | 65 | 35 |

The flow rate was 0.75 mL/min, detection UV at 260 nm, column temp. 50° C. The pH was 7.0.

Figure 20:
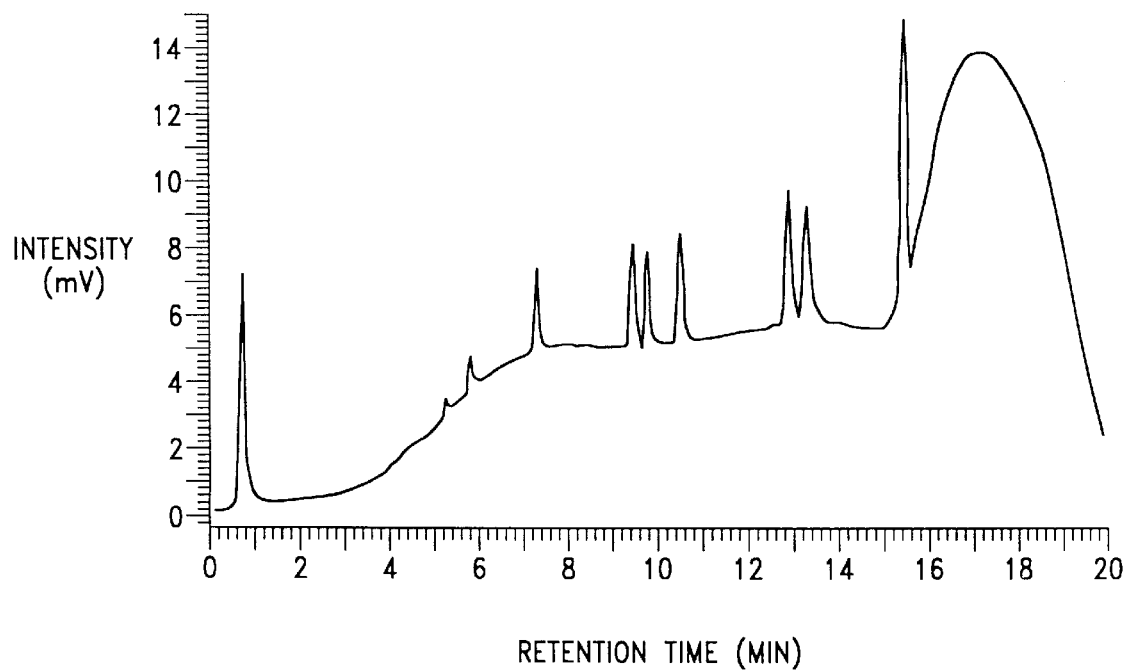
FIG. 20 is a MIPC separation of pUC18 DNA-HaeIII digestion fragments on a column containing nonporous 2.1 micron beads of underivatized poly(styrene-divinylbenzene).

As another example of this procedure using the same separation conditions as in FIG. 19, FIG. 20 is a high resolution separation of the standard DNA mixture on a column containing nonporous 2.1 micron beads of underivatized poly(styrene-divinylbenzene).

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

What is claimed is:

1. A method for enhancing the detection of a polynucleotide separated by Matched Ion Polynucleotide Chromatography comprising:
    a) covalently attaching a chemical tag to said polynucleotide to form a tagged polynucleotide,
    b) applying said tagged polynucleotide to a separation medium having a non-polar surface, wherein said separation medium is substantially free of multivalent cations capable of interfering with polynucleotide separation,
    c) eluting said tagged polynucleotide from said surface with a mobile phase containing a counterion agent and an organic solvent, and
    d) detecting said tagged polynucleotide, wherein said medium is characterized by having a DNA Separation Factor of at least 0.5.

2. The method of claim 1 wherein said tag comprises a fluorescent group.

3. The method of claim 2 wherein said fluorescent group is selected from the group consisting of 5-carboxyfluorescein, 2',7'-dimethoxy-4',5'-dichloro-6-carboxyfluorescein, N,N,N',N'-tetramethyl-6-carboxyrhodamine, 6-carboxy-X-rhodamine, Fluorescein, Rhodamine, BODIPY-TR-X, and Cascade Blue, and Alexa 350.

4. The method of claim 1 wherein said tag absorbs at a wavelength different from said polynucleotide.

5. The method of claim 4 wherein said tag is selected from the group consisting of porphyrin derivative, 5-carboxyfluorescein, 2',7'-dimethoxy4',5'-dichloro-6-carboxyfluorescein, N,N,N',N'-tetramethyl-6-carboxyrhodamine, 6-carboxy-X-rhodamine, Fluorescein, Rhodamine, BODIPY-TR-X, Cascade Blue, and Alexa 350.

6. The method of claim 1 wherein said medium comprises polymer beads having an average diameter of 0.5 to 100 microns and having a surface composition that is either unsubstituted or essentially completely substituted with a moiety selected from the group consisting of methyl, ethyl, hydrocarbon having from 23 to 1,000,000 carbons, and hydrocarbon polymer having from 23 to 1,000,000 carbons.

7. The method of claim 1 wherein said medium comprises beads having an average diameter of 0.5 to 100 microns, the beads comprising nonporous particles coated with a hydrocarbon or non-polar hydrocarbon substituted polymer, or particles having substantially all polar groups reacted with a non-polar hydrocarbon or substituted hydrocarbon group, wherein said particles are a member selected from the group consisting of silica, silica carbide, silica nitrite, titanium oxide, aluminum oxide, zirconium oxide, carbon, insoluble polysaccharide, and diatomaceous earth.

8. The method of claim 1 wherein said tagged polynucleotide comprises a PCR amplification product obtained by providing a PCR primer having a covalently bound tag during a PCR amplification wherein said tag is incorporated into said PCR amplification product.

9. A method for enhancing the detection of a polynucleotide separated by Matched Ion Polynucleotide Chromatography comprising:
    a) covalently attaching a chemical tag to said polynucleotide to form a tagged polynucleotide,
    b) applying said tagged polynucleotide to a separation bed of separation beads having non-polar surfaces, wherein said separation beads are substantially free of multivalent cations capable of interfering with polynucleotide separation, and wherein said separation bed is characterized by having a DNA Separation Factor of at least 0.5,
    c) eluting said tagged polynucleotide from said particles with a mobile phase containing a counterion agent and an organic solvent, and
    d) detecting said tagged polynucleotide, wherein steps (b) and (c) are performed in a system for separating a mixture of polynucleotide fragments comprising a chromatographic column having two ends, said column containing said separation bed of separation beads having non-polar surfaces held in the column between porous frits positioned at each end thereof, said column having an inlet, an injection valve in communication with said inlet through a flow path therebetween, mobile phase supply means in communication with said injection valve through at least one flow path therebetween, and multivalent cation capture resin, selected from the group consisting of cation exchange resin and chelating resin, positioned in said flow path, said multivalent cation capture resin being capable of removing multivalent cations from aqueous solutions, whereby any multivalent cation contaminants in said flow path are removed before said contaminants contact the separation bed.

10. A method for enhancing the detection of a polynucleotide separated by Matched Ion Polynucleotide Chromatography comprising:
    a) covalently attaching a chemical tag to said polynucleotide to form a tagged polynucleotide,
    b) applying said tagged polynucleotide to a separation bed of separation beads having non-polar surfaces, wherein said separation beads are substantially free of multivalent cations capable of interfering with polynucleotide separation, and wherein said separation bed is characterized by having a DNA Separation Factor of at least 0.5,
    c) eluting said tagged polynucleotide from said particles with a mobile phase containing a counterion agent and an organic solvent,
    d) detecting said tagged polynucleotide, wherein steps (b) and (c) are performed in a system for separating a mixture of polynucleotide fragments the system comprising a chromatographic column having two ends, said column containing a separation bed of separation beads having non-polar surfaces held in the column between porous frits positioned at each end thereof, said column having an inlet, an injection valve in communication with said inlet through a conduit, eluant supply means in communication with said injection valve through at least one conduit, wherein said porous frits, chromatographic column, injection valve, eluant supply means, and conduits have process solution-contacting surfaces which contact process solutions held therein or flowing therethrough, and wherein the process solution-contacting surfaces of said porous frits are material which does not release multivalent cations into aqueous solutions flowing therethrough.

11. A method for increasing the retention time of a polynucleotide separated by Matched Ion Polynucleotide Chromatography comprising:
   a) covalently attaching a chemical tag to said polynucleotide to form a tagged polynucleotide,
   b) applying said tagged polynucleotide to a separation medium having a non-polar surface, wherein said separation medium is substantially free of multivalent cations capable of interfering with polynucleotide separation, and wherein said separation bed is characterized by having a DNA Separation Factor of at least 0.5,
   c) eluting said tagged polynucleotide from said surface with a mobile phase containing a counterion agent and an organic solvent,
   d) detecting said tagged polynucleotide.

12. A method for enhancing the detection of a polynucleotide separated Matched Ion Polynucleotide Chromatography, comprising:
   a) contacting said polynucleotide with a reversible DNA-binding dye to form a complex between said polynucleotide and said reversible DNA-binding dye,
   b) applying said complex to a separation medium having a non-polar surface, wherein said separation medium is substantially free of multivalent cations capable of interfering with polynucleotide separation, and wherein said separation medium is characterized by having a DNA Separation Factor of at least 0.5,
   c) eluting said complex from said surface with a mobile phase containing a counterion agent and an organic solvent, and
   d) detecting said complex.

13. The method of claim 12 in which said reversible DNA-binding dye is selected from the group consisting of DNA intercalator dye and DNA groove binding dye.

14. The method of claim 12 in which said reversible DNA-binding dye is selected from the group consisting of PICO GREEN, ethidium bromide, propidium iodide, Acridine orange, 7-aminoactinomycin D, cyanine dye, Bisbenzimide, Benzoxanthene yellow, Netropsin, Indole dye, Imidazole dye, and Actinomycin D.

15. A method for the detection of a mutation in a sample double stranded DNA fragment, said method comprising:
   a) covalently attaching a chemical tag to said sample DNA fragment or a corresponding wild type fragment to form a tagged polynucleotide,
   b) hybridizing said sample DNA fragment with said corresponding wild type DNA fragment to form a mixture of homoduplexes and heteroduplexes if a mutation is present in said sample DNA fragment,
   c) applying the product of step (b) to a separation medium having a non-polar separation surface wherein said separation medium is substantially free of multivalent cations capable of interfering with polynucletide separation, and wherein said separation medium is characterized by having a DNA Separation Factor of at least 0.5,
   d) eluting said mixture with a mobile phase containing a counterion agent and an organic solvent where said eluting is carried out under conditions effective to at least partially denature said heteroduplexes and where said eluting results in the separation of said heteroduplexes from said homoduplexes, and
   e) monitoring said mobile phase during said eluting for the presence of tagged heteroduplex, wherein the presence of tagged heteroduplex indicates the presence of said mutation.

16. The method of claim 15 in which a different uniquely detectable tag is covalently attached to each strand of said sample DNA.

17. The method of claim 15 in which a different uniquely detectable chemical tag is covalently attached to each strand of said wild type fragment.

18. The method of claim 15 in which said wild type fragment in step (b) is tagged and the amount of said wild type fragment is added in excess of said sample DNA.

19. A method for increasing the melting temperature of a double stranded DNA as determined by temperature titration using Matched Ion Polynucleotide Chromatography, said method comprising:
   covalently binding a non-polar chemical tag to said DNA, to form a tagged polynucleotide, prior to said temperature titration,
   wherein said temperature titration is performed by (a) applying the tagged polynucleotide to a separation medium having a non-polar separation surface and that is substantially free of multivalent cations capable of interfering with polynucleotide separation, and wherein said separation medium is characterized by having a DNA Separation Factor of at least 0.5, (b) eluting the tagged polynucleotide from the surface with a mobile phase containing a counterion agent and an organic solvent, and (c) detecting the tagged polynucleotide, wherein steps (a) and (b) are performed at a plurality of temperatures above and below the melting temperature.

20. The method of claim 19 wherein said non-polar chemical tag comprises a hydrocarbon group, wherein said hydrocarbon group is selected from the group consisting of alkyl, cycloalkyl, aryl and arylalkyl groups.

21. The method of claim 19 wherein said non-polar tag comprises a fluorescent group.

22. The method of claim 19 wherein said non-polar tag is bound at an end of said DNA.

23. A method for detecting a covalently tagged polynucleotide separated by Matched Ion Polynucleotide Chromatography comprising:
   a) applying said tagged polynucleotide to a separation medium having a non-polar surface, wherein said separation medium is substantially free of multivalent cations capable of interfering with polynucleotide separation,
   b) eluting said tagged polynucleotide from said surface with a mobile phase containing a counterion agent and an organic solvent, and
   c) detecting said tagged polynucleotide, wherein said medium is characterized by having a DNA Separation Factor of at least 0.5.

24. The method of claim 23 wherein said tag comprises a fluorescent group.

25. The method of claim 23 wherein said tag absorbs at a wavelength different from said polynucleotide.

26. A method for detecting a complex comprising a polynucleotide bound to a reversible DNA-binding dye, as separated by Matched Ion Polynucleotide Chromatography, comprising:
   a) applying said complex to a separation medium having a non-polar surface, wherein said separation medium is substantially free of multivalent cations capable of interfering with polynucleotide separation, b) eluting said complex from said surface with a mobile phase containing a counterion agent and an organic solvent, and a) detecting said complex, wherein said medium is characterized by having a DNA Separation Factor of at least 0.5.

27. A method for enhancing the detection of a polynucleotide separated by Matched Ion Polynucleotide Chromatography comprising:
   a) covalently attaching a chemical tag to said polynucleotide to form a tagged polynucleotide,
   b) applying said tagged polynucleotide to a separation medium having a non-polar surface wherein said separation medium is substantially free of multivalent cations capable of interfering with polynucleotide separation,
   c) eluting said tagged polynucleotide from said surface with a mobile phase containing a counterion agent and an organic solvent, and
   d) detecting said tagged polynucleotide, wherein said medium is characterized by having a DNA Separation Factor of at least 0.5, wherein said medium comprises a polymeric monolith.

28. A method for enhancing the detection of a polynucleotide separated by Matched Ion Polynucleotide Chromatography comprising:
   a) covalently attaching a chemical tag to said polynucleotide to form a tagged polynucleotide,
   b) applying said tagged polynucleotide to a separation medium having a non-polar surface wherein said separation medium is substantially free of multivalent cations capable of interfering with polynucleotide separation,
   c) eluting said tagged polynucleotide from said surface with a mobile phase containing a counterion agent and an organic solvent, and
   d) detecting said tagged polynucleotide, wherein said medium is characterized by having a DNA Separation Factor of at least 0.5, wherein said medium comprises a derivatized silica gel monolith.

29. A method for increasing the retention time of a polynucleotide separated by Matched Ion Polynucleotide Chromatography comprising:
   a) covalently attaching a chemical tag to said polynucleotide to form a tagged polynucleotide,
   b) applying said tagged polynucleotide to a separation medium having a non-polar surface wherein said separation medium is substantially free of multivalent cations capable of interfering with polynucleotide separation,
   c) eluting said tagged polynucleotide from said surface with a mobile phase containing a counterion agent and an organic solvent,
   d) detecting said tagged polynucleotide, wherein said medium is characterized by having a DNA Separation Factor of at least 0.5, wherein said chemical tag is non-polar, wherein said tag comprises a hydrocarbon group, wherein said hydrocarbon group is selected from the group consisting of alkyl, cycloalkyl, aryl and arylalkyl groups.

* * * * *